United States Patent
Hagiwara et al.

(10) Patent No.: US 9,241,929 B2
(45) Date of Patent: Jan. 26, 2016

(54) PROPHYLACTIC OR AMELIORATING AGENT FOR GENETIC DISEASES

(75) Inventors: Masatoshi Hagiwara, Kyoto (JP); Masafumi Matsuo, Hyogo (JP); Naoyuki Kataoka, Kyoto (JP); Atsushi Nishida, Hyogo (JP)

(73) Assignees: Masatoshi Hagiwara, Kyoto (JP); Masafumi Matsuo, Hyogo (JP)

( * ) Notice: Subject to any disclaimer, the term of this patent is extended or adjusted under 35 U.S.C. 154(b) by 95 days.

(21) Appl. No.: 13/805,151

(22) PCT Filed: Jun. 27, 2011

(86) PCT No.: PCT/JP2011/003655
§ 371 (c)(1),
(2), (4) Date: Dec. 18, 2012

(87) PCT Pub. No.: WO2012/001941
PCT Pub. Date: Jan. 5, 2012

(65) Prior Publication Data
US 2013/0102644 A1  Apr. 25, 2013

(30) Foreign Application Priority Data
Jun. 28, 2010 (JP) ................................ 2010-146699

(51) Int. Cl.
| A61K 31/425 | (2006.01) |
| A61K 31/428 | (2006.01) |
| C07K 14/47 | (2006.01) |
| C07D 277/64 | (2006.01) |
| C12N 9/12 | (2006.01) |

(52) U.S. Cl.
CPC ............ *A61K 31/428* (2013.01); *C07D 277/64* (2013.01); *C07K 14/4707* (2013.01); *C07K 14/4708* (2013.01); *C12N 9/12* (2013.01)

(58) Field of Classification Search
CPC ............ A61K 31/428; C07K 14/4707; C07K 14/4708; C07D 277/64; C07D 277/66
USPC .......................................... 514/365, 366, 367
See application file for complete search history.

(56) References Cited

U.S. PATENT DOCUMENTS

| 7,786,151 | B2 * | 8/2010 | Hagiwara et al. ............. 514/367 |
| 8,501,713 | B2 * | 8/2013 | Wynne et al. .................... 514/80 |
| 2005/0171026 | A1 * | 8/2005 | Hagiwara et al. ................ 514/23 |
| 2011/0195932 | A1 * | 8/2011 | Wynne et al. .................... 514/80 |

FOREIGN PATENT DOCUMENTS

| JP | 2009-521408 A | 6/2009 |
| WO | 2007102861 A2 | 9/2007 |
| WO | 2009087238 A2 | 7/2009 |

OTHER PUBLICATIONS

Behm-Ansmant et al., "mRNA quality control: An ancient machinery recognizes and degrades mRNAs with nonsense codons", 2007, FEBS Letters, vol. 581: 2845-2853.*
Keeling et al., "Suppression of nonsense mutations as a therapeutic approach to treat genetic diseases", Nov./Dec. 2011, Wiley Interdisciplinary Reviews: RNA, vol. 2, Issue 6; pp. 837-852.*
Keeling et al., "Suppression of premature termination codons as a therapeutic approach", Sep./Oct. 2012, Critical Reviews in Biochemistry and Molecular Biology; 47(5): 444-463.*
Bidou et al., "Sense from nonsense: therapies for premature stop codon diseases", Nov. 2012, Trends in Molecular Medicine, vol. 18, No. 11; pp. 679-688.*
Alter, J., et al., "Systemic delivery of morpholino oligonucleotide restores dystrophon expression bodywide and improves dystrophic pathology," Nature Medicine (2006) 12:2 175-177.
Aartsma-Rus, A, et al., "Less is more: therapeutic exon skipping for Duchenne muscular dystrophy," (2009) vol. 8 www.thelancet.com/neurology.
Disset, A., et al., "An exon skipping-associated nonsense mutation in the dystrophin gene uncovers a complex interplay between multiple antagonistic splicing elements," Human Molecular Genetics (2006) 15:6 999-1013.
Hagiwara, M., "Challenge to intractable diseases by chemical biology," The Japanese Pharmacological Society (2009) 120:14.
Hirawat, S., et al., "Safety, Tolerability, and Pharmacokinetics of PTC124, a Nonaminoglycoside Nonsense Mutation Suppressor, Following Single- and Multiple-Dose Administration to Healthy Male and Female Adult Volunteers," J Clin Pharmacol (2007) 47:430-444.
Kinali, M., et al., "Local restoration of dystrophin expression with the morpholino oligomer AVI-4658 in Duchenne muscular dystrophy: a single-blind, placebo-controlled, dose-escalation, proof-of-concept study," www.thelancet.com/neurology vol. 8 (2009).
Koenig, M., et al., "The Complete Sequence of Dystrophin Predicts a Rod-Shaped Cytoskeletal Protein," Cell (1988) 53:219-228.
Matsuo, M., "Becker muscular dystrophy resulted from exon skipping that removes nonsense mutation," Gene & Medicine (1999) 3:2 86-90.
Monaco, A.P., "An Expanation for the Phenotypic Differences between Patients Bearing Partial Deletions of the DMD Locus," Genomics (1988) 2:90-95.

(Continued)

*Primary Examiner* — My-Chau T Tran
(74) *Attorney, Agent, or Firm* — Chainey P. Singleton; Edwin S. Flores; Chalker Flores, LLP

(57) ABSTRACT

An object of the present invention is to provide a prophylactic or ameliorating agent for a genetic disease that is caused by a mutation in an exon of a gene and is capable of forming a functional truncated protein by skipping of the exon comprising the mutation. The prophylactic or ameliorating agent used in the present invention is a prophylactic or ameliorating agent for a genetic disease that is caused by a mutation in an exon of a gene and is capable of forming a functional truncated protein by skipping of the exon comprising the mutation, wherein the prophylactic or ameliorating agent contains a compound having a molecular weight of 1500 or lower.

10 Claims, 7 Drawing Sheets

(56) References Cited

OTHER PUBLICATIONS

Muraki, M., et al., "Manipulation of Alternative Splicing by a Newly Developed Inhibitor of Clks," The Journal of Biological Chemistry (2004) 279:23 24246-24254.

Nishida, A., et al., "Chemical treatment enhances skipping of a mutated exon in the dystrophon gene," Nature Communications (2011) 2:308 1-8.

O'Leary, D. A., et al., "Identification of Small Molecule and Genetic Modulators of AON-Induced Dystrophin Exon Skipping by High-Throughput Screening," (2009) 4:12 1-15.

Pramono, Z. A. D., et al., "Induction of Exon Skipping of the Dystrophin Transcript in Lymphoblastoid Cells by Transfecting an Antisense Oligodeoxynucleotide Complementary to an Exon Recognition Sequence," Biochemical and Biophysical Research Communications 226:445-449.

Takeshima, Y., et al., "Modulation of in Vitro Splicing of the Upstream Intron by Modifying an Intra-Exon Sequence Which is Deleted from the Dystrophin Gene in Dystrophin Kobe," J. Clin. Invest. (41995) 95:515-520.

Takeshima, Y., et al., "Intravenous Infusion of an Antisense Oligonecleotide Results in Exon Skipping in Muscle Dystrophin mRNA of Duchenne Muscular Dystrophy," Pediatric Research (2006) 59:5 690-694.

van Deutekom, J. C., et al., "Local Dystrophin Restoration with Antisense Oligonucleotide PRO051," N Engl J Med 357:26 2677-2686.

Welch, E. M., et al., "PTC124 targets genetic disorders caused by nonsense mutations," Nature Letters (2007) 447:87-93.

Yomoda, J., et al., "Combination of Clk family kinase and SRp75 modulates alte4rnative splicing of Adenovirus E1A," Genes to Cells (2008) 13:233-244.

International Search Report PCT/JP2011/003655 Jun. 28, 2010.

International Preliminary Report on Patentability PCT/JP2001/003655 Dated Jan. 24, 2013.

Hu, Yihong, et al., "Guanine Analogues Enhance Antisense Oligonucleotide-induced Exon Skipping in Dystrophin Gene in Vitro and in Vivo," (Apr. 2010) Molecular Therapy vol. 18, No. 4, pp. 812-818.

Stoilov, Peter, et al., "A high-throughput screening strategy identifies cardiotonic steroids as alternative splicing modulators," (Aug. 12, 2008) PNAS vol. 105, No. 32, pp. 11218-11223.

Extended European Search Report, EP 11800411.8 Dated Nov. 13, 2013.

* cited by examiner a b c

PROPHYLACTIC OR AMELIORATING AGENT FOR GENETIC DISEASES

TECHNICAL FIELD

The present invention relates to a prophylactic or ameliorating agent for a genetic disease that is caused by a mutation in an exon of a gene and is capable of forming a functional truncated protein by skipping of the exon comprising the mutation, wherein the prophylactic or ameliorating agent contains a compound having a molecular weight of 1500 or lower.

BACKGROUND ART

Muscular dystrophy is a generic name for genetic muscular diseases that show the gradual progression of muscle atrophy or weakness resulting from the repeated cycles of the breakdown or degeneration (necrosis) and regeneration of muscle fibers. Among these diseases, progressive muscular dystrophy is well known. Duchenne muscular dystrophy (DMD), one type of progressive muscular dystrophy, is the most common form of the muscular dystrophy and is caused by mutations in the dystrophin gene, which is located on the X chromosome (see non-patent document 1). Reportedly, DMD patients typically die of heart failure or respiratory failure in their 20s due to progressive muscle atrophy that began in early childhood.

The dystrophin protein (hereinafter, also simply referred to as "dystrophin"), which is located at the cytoplasmic face of the sarcolemma, plays a role in, for example, structurally maintaining muscle cells by conveying mechanical energy generated by actin-myosin-driven muscle contraction to the sarcolemma, its surrounding connective tissues, tendons, etc., in a balanced manner, and regulatorily preventing excessive impact from being applied thereto. In the case of DMD patients, their muscle fibers contain no or only scarce dystrophin protein due to mutations in the dystrophin genes. The sarcolemma is thus disrupted as a result of muscle contraction, leading to the entrance of a larger-than-normal amount of calcium ions into the muscle fibers. Excessive calcium activates enzymes, such as calpains or proteases, which break down the muscle or induce apoptosis. As a result, fibroblasts are activated to form fibrotic scar tissues, which in turn impede the regeneration of muscle cells and accelerate muscle atrophy.

Becker muscular dystrophy (BMD), another type of progressive muscular dystrophy, is also caused by mutations in the dystrophin gene, but typically affects only adults. Its symptoms also progress more slowly than DMD. DMD and BMD differ in the severity of symptoms and the rate of progression thereof, though these diseases are both caused by mutations in the dystrophin gene. This difference between DMD and BMD is explained by the reading frame rule. A premature termination codon (PTC) mutation (nonsense mutation) in dystrophin mRNA usually brings about a grave DMD phenotype (Duchenne type), whereas a mutation that does not alter the original reading frame of dystrophin mRNA (in-frame mutation) results in a milder BMD phenotype (Becker type) (see non-patent document 2). Unexpectedly, in spite of the fact that some mild BMD patients have a nonsense mutation in their dystrophin genes, the skipping of an exon comprising this nonsense mutation reportedly yields new in-frame dystrophin mRNA (see non-patent documents 3 to 6). Dystrophin (truncated dystrophin) encoded by this dystrophin mRNA lacking some such exons by skipping is shorter than normal dystrophin, but still has, to some extent, the function of structurally maintaining muscle cells. The resulting muscular dystrophy exhibits relatively mild symptoms. Also, muscle atrophy progresses at a relatively slow rate.

The fundamental therapy of muscular dystrophy remains to be established. Only symptomatic treatment for heart failure or respiratory disorder has previously been practiced, in addition to functional training or stretch to prevent joint contracture. Novel therapy for DMD, however, has been developed by the present inventors or other researchers in recent years and has encouraged expectations. This therapy is a method involving inducing exon skipping using an antisense oligonucleotide (AON) against dystrophin mRNA to convert a DMD phenotype to a BMD phenotype so that symptoms are relieved (non-patent document 3). Some different types of AONs were designed against any of splice sites or splicing-enhancing elements in order to induce exon skipping in the cells of DMD patients. These AONs successfully repaired the reading frame of dystrophin mRNA. For example, AON against an exonic splicing enhancer (ESE) in exon 19 caused the skipping of exon 19 in the cells of the DMD patients to observably form truncated dystrophin (see non-patent documents 3 to 5). Alternatively, AON against exon 51 is also often used for such patient-derived cells. These AONs are currently at the stage of clinical study (see non-patent documents 6 to 8).

Unfortunately, such AONs must be injected intramuscularly or intravenously on a regular basis. This becomes undesirable burdensome to patients. Also, the preparation of AONs in large amounts disadvantageously costs a great deal of money. In addition, when mdx mice (muscular dystrophy model mice) were treated with AON, dystrophin expression made a recovery to some extent in the skeletal muscles, but was difficult to recover in the hearts (non-patent document 9). Thus, low molecules that regulate exon skipping have been strongly demanded from a clinical standpoint. According to the reports, PTC124 (registered trademark) (3-[5-(2-fluorophenyl)-1,2,4-oxadiazol-3-yl]benzoic acid), a low-molecular-weight non-aminoglycoside nonsense mutation suppressor compound, is capable of treating some DMD patients having a nonsense mutation (non-patent documents 10 and 11) and is currently under phase IIb clinical trial in the USA, etc. PTC124 is a therapeutic drug that induces ribosome to read through a premature termination codon (PTC) during translation so that the expression of full-length functional dystrophin is recovered to some extent. Its influence on the nonsense mutation-dependent mRNA decay mechanisms of the other genes is still uncertain.

The present inventors have identified a Cdc-like kinase (Clk)-specific kinase inhibitor TG003 (compound represented by the general formula (1) described later wherein $R_1$ and $R_2$ each represent a methyl group; and $R_3$ represents a methoxy group). The compound TG003 influences splicing both in vitro and in vivo (see non-patent documents 12 and 13). The patent application (see patent document 1) in which the present inventors are involved discloses that TG003 has the effect of regulating alternative splicing mediated by the phosphorylation of SR protein and that diseases such as cancer may be prevented or treated using this effect. It has been unknown so far that TG003 is capable of promoting the skipping of an exon in the dystrophin gene.

PRIOR ART DOCUMENTS

Patent Document

Patent Document 1: U.S. Patent Application Publication No. 20050171026

Non-Patent Documents

Non-patent Document 1: Cell (1988) 53, 219-228
Non-patent Document 2: Genomics (1988) 2, 90-95
Non-patent Document 3: Pediatr Res (2006) 59, 690-694
Non-patent Document 4: Biochem Biophys Res Commun (1996) 226, 445-449
Non-patent Document 5: J Clin Invest (1995) 95, 515-520
Non-patent Document 6: Lancet Neurology (2009) 8, 873-875
Non-patent Document 7: The New England Journal of Medicine (2007) 357, 2677-2686
Non-patent Document 8: Lancet Neurology (2009) 8, 918-928
Non-patent Document 9: Nature Medicine (2006) 12, 175-177
Non-patent Document 10: J Clin Pharmacol (2007) 47, 430-444
Non-patent Document 11: Nature (2007) 447, 87-91
Non-patent Document 12: The Journal of Biological Chemistry (2004) 279, 24246-24252
Non-patent Document 13: Genes Cells (2008) 13, 233-244

SUMMARY OF THE INVENTION

Object to be Solved by the Invention

An object of the present invention is to provide a prophylactic or ameliorating agent for a genetic disease that is caused by a mutation in an exon of a gene and is capable of forming a functional truncated protein by skipping of the exon comprising the mutation, wherein the prophylactic or ameliorating agent contains a compound having a molecular weight of 1500 or lower.

Means to Solve the Object

The present inventors have analyzed more than 400 muscular dystrophy patients for mutations in their dystrophin genes and consequently discovered patients who have BMD-type symptoms, though they have, in exon 31, a nonsense mutation presumed to cause a grave DMD phenotype according to the reading frame rule described in Background Art. As a result of analyzing mRNAs of the dystrophin genes in these patients, it has been confirmed that mature mRNAs encoding functional truncated dystrophin are partially produced due to the skipping of exon 31 induced by the nonsense mutation in this exon 31. Thus, the present inventors have searched for a low-molecular-weight compound that promotes exon skipping and consequently found that the Clk-specific inhibitor TG003 is capable of promoting the skipping of exon 31 or exon 27 of the endogenous dystrophin gene in a dose-dependent manner and potentiating the production of functional truncated dystrophin in patient-derived cells. On the basis of these findings, the present invention has been completed.

Specifically, the present invention relates to: (1) a prophylactic or ameliorating agent for a genetic disease that is caused by a mutation in an exon of a gene and is capable of forming a functional truncated protein by skipping of the exon comprising the mutation, wherein the prophylactic or ameliorating agent contains a compound having a molecular weight of 1500 or lower; (2) the prophylactic or ameliorating agent according to (1), wherein the compound has a splicing regulatory action; (3) the prophylactic or ameliorating agent according to (1) or (2), wherein the compound has an inducing or promoting effect on the skipping of the exon comprising the mutation; (4) the prophylactic or ameliorating agent according to any one of (1) to (3), wherein the compound is a Cdc-like kinase inhibitory compound; (5) the prophylactic or ameliorating agent according to (4), wherein the Cdc-like kinase inhibitory compound is represented by the following general formula (1):

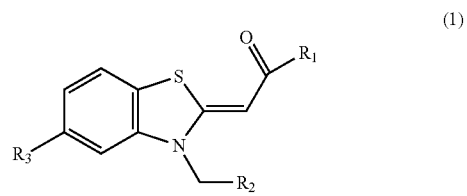

(1)

[wherein $R_1$ and $R_2$ each independently represent a linear or branched $C_1$-$C_{10}$ hydrocarbon group; and $R_3$ represents a methoxy group, an ethoxy group, an acetoxy group, or a halogen atom];
(6) the prophylactic or ameliorating agent according to any one of (1) to (5), wherein the mutation is a nonsense mutation; (7) the prophylactic or ameliorating agent according to (6), wherein the nonsense mutation suppresses exonic splicing enhancer activity in the gene and/or enhances exonic splicing silencer activity in the gene; (8) the prophylactic or ameliorating agent according to any one of (1) to (7), wherein the gene is dystrophin gene, wherein the functional truncated protein is a functional truncated dystrophin protein, and the genetic disease is Duchenne muscular dystrophy; (9) the prophylactic or ameliorating agent according to (8), wherein the exon of the dystrophin gene is exon 31 or exon 27 of the dystrophin gene; and (10) the prophylactic or ameliorating agent according to (9), wherein the mutation in exon 31 of the dystrophin gene is a nonsense mutation of guanine to thymine at nucleotide No: 4303 in the polynucleotide sequence of SEQ ID NO: 1, and the mutation in exon 27 is an out-of-frame mutation that deletes guanine at nucleotide No. 3613 in the polynucleotide sequence of SEQ ID NO: 1.

Effect of the Invention

According to the present invention, the skipping of an exon of a gene comprising a mutation responsible for a genetic disease can be induced or promoted to thereby induce or enhance the expression of a functional truncated protein. As a result, the genetic disease can be prevented or ameliorated. The compound having a molecular weight of 1500 or lower, used in the present invention, is a low molecule and is excellent in tissue migration, etc. This compound can therefore be expected to have a sufficient prophylactic or ameliorating effect even on organs, such as the heart, on which conventional high-molecular-weight AON does not exhibit a sufficient effect. In addition, the mutation targeted by the present invention is not limited to a nonsense mutation. Thus, its application to diverse mutations responsible for genetic diseases can also be expected.

BRIEF DESCRIPTION OF DRAWINGS

FIG. 1(a) shows a point mutation found in the dystrophin gene of patient No. KUCG797. The position of the c.4303G>T (p.Glu1435X) mutation in exon 31 is indicated by the bar. The DNA sequences of its flanking intron regions and the codon thus mutated are also shown therein. In FIG. 1(b), panels e to g show results of examining dystrophin expression in the patient by an immunohistochemical method, while panels b to d show results of examining dystrophin expression in a healthy person by an immunohistochemical method. Panels e and b show the results of staining with DYS2. Panels f and c show the results of staining with DYS3. Panels g and d show the results of staining with MANDYS1. Scale bar=60 μM. FIG. 1(c) shows results of analyzing, on agarose gels, RT-PCR products obtained from the muscles of the control and the patient. The left lane (M) represents the results obtained using a DNA size marker digested with φX174-HaeIII. The central lane (Control) represents the results obtained using healthy person-derived total RNA as a template. The right lane (Patient) represents the results obtained using KUCG797-derived total RNA as a template. The DNA sequences of these bands were analyzed, and the structures of these PCR products are schematically shown, together with their nucleotide lengths, on the right side of the panel. The numbered box represents an exon number of the dystrophin gene. The length of the DNA size marker is indicated by the nucleotide length on the left side of the panel. FIG. 1(d) shows results of sequencing the smaller-size amplification product of FIG. 1(c). FIG. 1(e) shows a schematic diagram of a hybrid minigene plasmid comprising either wild-type (WT) or mutant (c.4303G>T) exon 31 of the dystrophin gene. The box and the line on the right side of the panel represent an exon and an intron, respectively. FIG. 1(f) shows results of electrophoresing, on agarose gels, RT-PCR products or the like of mutant mRNA collected from H492-dys Ex31 m/Hela or wild-type mRNA collected from H492-dys Ex31w/Hela. The leftmost lane (M) represents the results obtained using a DNA size marker digested with φX174-HaeIII. The second left lane (w) represents the results obtained using H492-dys Ex31w/ Hela-derived total RNA as a template. The third left lane (m) represents the results obtained using H492-dys Ex31 m/Hela-derived total RNA as a template. The structures of these PCR products are schematically shown on the right side of the panel. The nucleotide lengths of the DNA size marker and the PCR products are shown on the left and right sides, respectively, of the panel. The second and third right lanes represent results of electrophoresing, on agarose gels, templates treated by RT-PCR in the same way except that reverse transcriptase (RT) was not added. The second right lane (w) represents the results obtained using H492-dys Ex31w/Hela-derived total RNA as a template. The rightmost lane (m) represents the results obtained using H492-dys Ex31 m/Hela-derived total RNA as a template.

FIG. 2(a) shows results of predicting RNA-binding candidate proteins capable of binding to wild-type exon 31 (left panel) or c.4303G>T exon 31 (right panel) of the dystrophin gene using the SpliceAid program. A sequence, such as an exonic splicing enhancer (ESE) motif, which easily defines an exon, was given a positive score. According to the same criteria, a target sequence that easily defines an intron, i.e., an exonic splicing silencer (ESS) motif, was given a negative score. In both right and left panels, the c.4303G>T mutated nucleotide is highlighted. Two types of proteins (SRp30c/SRSF9 and hnRNP A1) having scores largely changed depending on the presence or absence of this mutation are indicated by the open box. A surrounding sequence highly homologous to a SELEX consensus sequence for SRp30c/SRSF9 (left panel) or hnRNP A1 (right panel) is underlined. FIG. 2(b) shows the alignment between the SELEX consensus sequence for SRp30c/SRSF9 or hnRNP A1 and the exon 31 sequence. The left panel shows the homology between wild-type exon 31 RNA and the SRp30c/SRSF9 SELEX consensus sequence. The symbol R represents a purine residue. The right panel shows the RNA sequence homology between c.4303G>T mutant exon 31 and the hnRNP A1 SELEX consensus sequence. The symbol W represents A or U. In both panels, the vertical bar links the same bases. In both panels, the c.4303G>T mutated nucleotide is emphasized by the open box.

FIG. 3(a) is a diagram showing results of gel mobility shift assay conducted on GST-hnRNP A1 and dystrophin exon 31 RNA. Lanes 3 to 5 show the results obtained using 100, 200, and 400 ng, respectively, of GST-hnRNP A1 and wild-type exon 31 RNA of the dystrophin gene. Lanes 8 to 10 show the results obtained using 100, 200, and 400 ng, respectively, of GST-hnRNP A1 and mutant exon 31 RNA of the dystrophin gene. Lanes 2 and 7 represent the results obtained using only GST. Lanes 1 and 6 show the position to which the RNA itself migrated on the gel (indicated by "Free RNA" on the right side of the panel). The complex of hnRNP A1 and RNA is indicated by "Bound RNA. " FIG. 3(b) shows results of in vitro splicing assay on a dystrophin mRNA precursor comprising exon 31. Lanes 1 to 5 represent the results obtained using linearized pCDC-dys Ex31w as an in vitro transcription template and incubation times of 0, 15, 30, 60, and 90 minutes, respectively. Lanes 6 to 10 represent the results obtained using linearized pCDC-dys Ex31m as an in vitro transcription template and incubation times of 0, 15, 30, 60, and 90 minutes, respectively. The structures of the mRNA precursor and two different mRNAs are shown on the right side of the panel. The numbered box represents an exon, while the line between the boxes represents an intron. Exons 14 and 15 are chicken δ-crystallin exons derived from a CDC mRNA precursor. Dystrophin mRNA comprising exon 31 (filled circle) was produced more efficiently by the CDC-dys Ex31 WT mRNA precursor than the CDC-dys Ex31 c.4303G>T mRNA precursor. FIG. 3(c) shows results of cell-based analysis of splicing conducted using a minigene in order to examine the influence of overexpression of some RNA-binding proteins on the skipping and inclusion of mutant exon 31. The leftmost lane (M) represents the results obtained using a DNA size marker digested with φX174-HaeIII. The second left lane (mock) represents the results obtained using H492-dys Ex31 m/Hela-derived total RNA as a template. The third left lane (SRp30c/SRSF9) represents the results obtained using H492-dys Ex31m.Flag-SRp30c/Hela-derived total RNA as a template. The second right lane (SRp75/SRSF4) represents the results obtained using H492-dys Ex31m.Flag-SRp75/Hela-derived total RNA as a template. The rightmost lane (hnRNP A) represents the results obtained using H492-dys Ex31m.Flag-hnRNP A1 plasmid/Hela-derived total RNA as a template. The nucleotide lengths of the DNA size marker and the PCR products are shown on the left and right sides, respectively, of the panel. FIG. 3(d) shows an exon skip/inclusion ratio calculated from the results of FIG. 3(c). The graph shows the mean and standard deviation of the ratios obtained from three individual experiments. *P<0.005.

FIG. 4(a) shows results of cell-based analysis of splicing conducted using H492-dys Ex31 m/Hela in order to examine the influence of various compounds on exon 31 skipping. The leftmost lane (M) represents the results obtained using a DNA size marker digested with φX174-HaeIII. The second left lane (DMSO) represents the results obtained using H492-dys Ex31 m/Hela treated with DMSO. The third left lane (TG003) represents the results obtained using H492-dys Ex31 m/Hela treated with TG003. The rightmost lane (SRPIN340) represents the results obtained using H492-dys Ex31 m/Hela treated with SRPIN340. The nucleotide lengths of the DNA size marker and the PCR products are shown on the left and right sides, respectively, of the panel. FIG. 4(b) shows an exon skip/inclusion ratio calculated from the results of FIG. 4(a). The graph shows the mean and standard deviation of the ratios obtained from three individual experiments. *P<0.0001. FIG. 4(c) shows results of cell-based analysis of splicing conducted using H492-dys Ex31 m/Hela as well as H492-dys Ex31w/Hela in order to examine whether TG003, which promotes the mutant exon 31 skipping, promotes the skipping of wild-type exon 31. The first to sixth left lanes represent the results obtained using H492-dys Ex31w/Hela treated with TG003 at a concentration (μM) shown in the upper region of the panel. The first to sixth right lanes represent the results obtained using H492-dys Ex31 m/Hela treated with TG003 at a concentration (μM) shown in the upper region of the panel. The central lane (M) represents the results obtained using a DNA size marker digested with φX174-HaeIII. FIG. 4(d) shows an exon skip/inclusion ratio calculated from the results of FIG. 4(c). The graph shows the mean and standard deviation of the ratios obtained from three individual experiments.

FIG. 5(a) shows results of cell-based analysis of splicing conducted using H492-dys Ex27 m/Hela and H492-dys Ex27w/Hela. The first to sixth left lanes represent the results obtained using H492-dys Ex27w/Hela treated with TG003 at a concentration (μM) shown in the upper region of the panel. The first to sixth right lanes represent the results obtained using H492-dys Ex27 m/Hela treated with TG003 at a concentration (μM) shown in the upper region of the panel. The central lane (M) represents the results obtained using a DNA size marker digested with φX174-HaeIII. FIG. 5(b) shows an exon skip/inclusion ratio calculated from the results of FIG. 5(a). The graph shows the mean and standard deviation of the ratios obtained from three individual experiments.

FIG. 6(a) shows results of cell-based analysis of splicing conducted using primary cultured cells of the patient muscle treated with varying amounts of TG003. The leftmost lane (M) represents the results obtained using a DNA size marker digested with φX174-HaeIII. The second to seventh left lanes represent the results obtained using primary cultured cells treated with TG003 at a concentration (μM) shown in the upper region of the panel. The DNA size marker is schematically shown on the left side of the panel, while the nucleotide lengths and structures of the PCR products are schematically shown on the right side of the panel. The numbered box on the right side of the panel represents an exon number of the dystrophin gene. FIG. 6(b) shows an exon skip/inclusion ratio calculated from the results of FIG. 6(a). The graph shows the mean and standard deviation of the ratios obtained from two individual experiments. FIG. 6(c) shows results of Western blotting analysis conducted on the expression of dystrophin in patient-derived cells treated with TG003. The upper panel (dystrophin (C-terminal)) represents the results obtained using an antibody against the C terminus of dystrophin. The central panel (dystrophin (Exon 31/32)) represents the results obtained using an antibody against a region corresponding to dystrophin exon 31. The lower panel (desmin) represents the results obtained using an anti-desmin antibody. The left lane (Control) represents the results obtained using a positive control. The central lane (0) represents the results obtained using patient-derived cells untreated with TG003. The right lane (7) represents the results obtained using patient-derived cells treated with TG003. The results of the lower panel demonstrated that substantially the same numbers of cells were used in this Western blotting analysis.

MODE OF CARRYING OUT THE INVENTION

Figure 1:
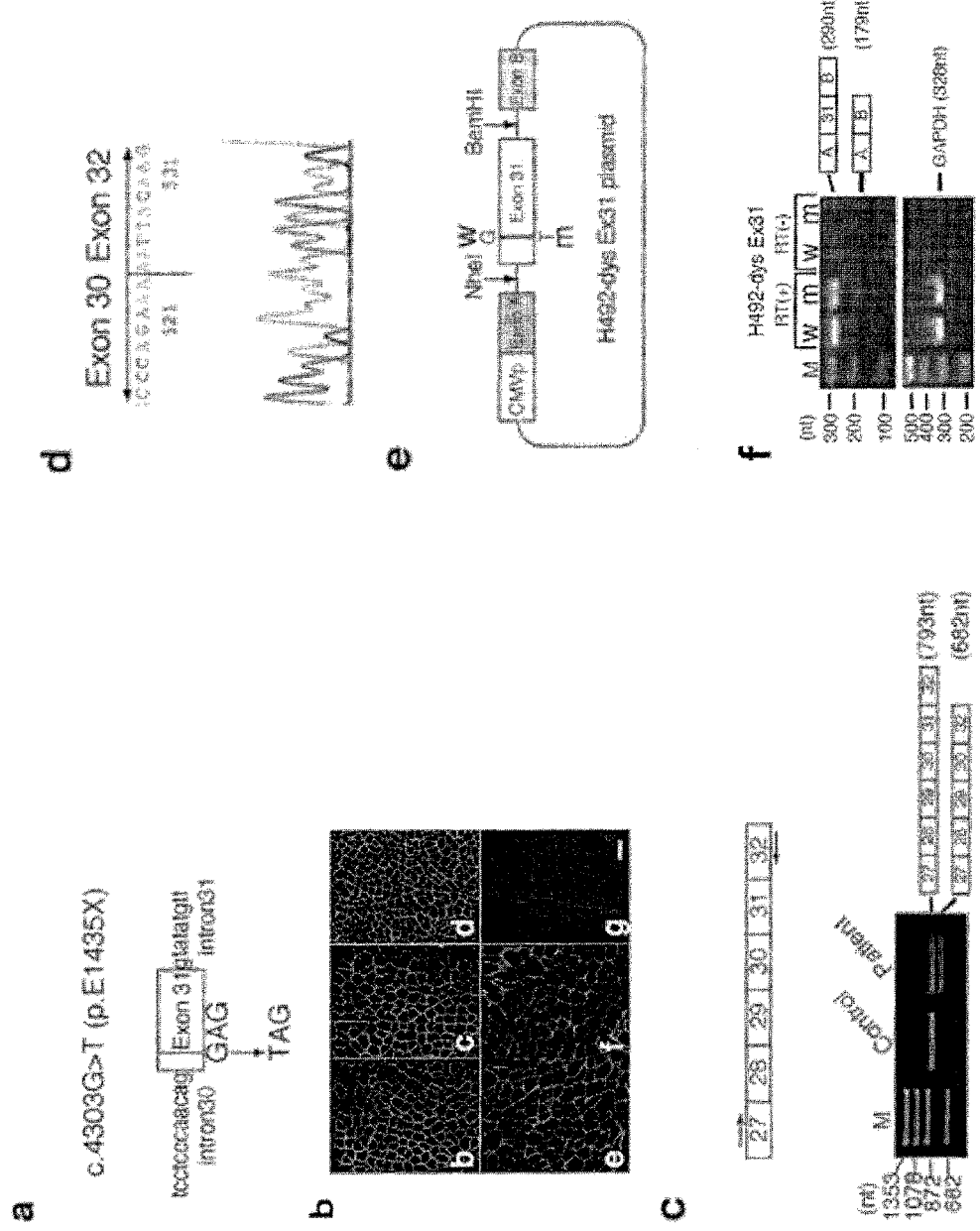
FIG. 1 is a diagram showing the manner in which a point mutation in exon 31 of the dystrophin gene in a patient causes exon skipping, which in turn repairs the open reading frame (ORF) of the truncated dystrophin gene.

1. Prophylactic or Ameliorating Agent of the Present Invention

The prophylactic or ameliorating agent of the present invention is not particularly limited as long as the prophylactic or ameliorating agent is a prophylactic or ameliorating agent for a genetic disease (hereinafter, also referred to as a "genetic disease targeted by the present invention") that is caused by a mutation in an exon of a gene and is capable of forming a functional truncated protein by skipping of the exon comprising the mutation (hereinafter, also simply referred to as a "mutant exon"), wherein the prophylactic or ameliorating agent contains a compound having a molecular weight of 1500 or lower (hereinafter, also referred to as a "compound according to the present invention"). Preferably, the compound has a molecular weight of 1000 or lower, more preferably 700 or lower, even more preferably 500 or lower, further preferably 300 or lower. Alternatively, the prophylactic or ameliorating agent of the present invention may contain two or more types of compounds according to the present invention in combination.

The compound according to the present invention is not particularly limited as long as the compound exerts a prophylactic and/or ameliorating effect (hereinafter, also referred to as a "prophylactic or ameliorating effect according to the present invention") on the genetic disease targeted by the present invention. Examples thereof can preferably include compounds having a splicing regulatory action, more preferably compounds having an inducing and/or promoting effect on the skipping of the mutant exon (hereinafter, also referred to as a "skipping-inducing or promoting effect according to the present invention"), even more preferably compounds having an effect of inducing and/or promoting the skipping of the mutant exon and inducing and/or enhancing the expression of the functional truncated protein (hereinafter, also referred to as a "functional truncated protein expression-inducing or enhancing effect according to the present invention"), further preferably Clk inhibitory compounds. Examples of the Clk inhibitory compounds can preferably include compounds represented by the general formula (1) [wherein $R_1$ and $R_2$ each independently represent a linear or branched $C_1$-$C_{10}$ hydrocarbon group; and $R_3$ represents a methoxy group, an ethoxy group, an acetoxy group, or a halogen atom], particularly preferably TG003 (compound represented by the general formula (1) wherein $R_1$ and $R_2$ each represent a methyl group; and $R_3$ represents a methoxy group). These compounds represented by the general formula (1) can be synthesized by, for example, a method described in patent document 1 mentioned above.

The prophylactic effect on the genetic disease targeted by the present invention (hereinafter, also referred to as a "prophylactic effect of the present invention") encompasses the effect of suppressing the onset of the genetic disease or the effect of delaying the onset of the genetic disease. The ameliorating effect on the genetic disease targeted by the present invention (hereinafter, also referred to as an "ameliorating effect of the present invention") encompasses the effect of ameliorating symptoms of the genetic disease as well as the effect of delaying the rate of aggravation of the symptoms compared with a case to which the prophylactic or ameliorating agent of the present invention is not administered.

Whether or not a certain compound has the prophylactic or ameliorating effect of the present invention can be confirmed by a method comprising, for example: step A of administering the test compound to a model mammal of the genetic disease targeted by the present invention (i.e., a model mammal (preferably, a model non-human mammal) having a mutation responsible for the genetic disease targeted by the present invention); step B of confirming symptoms of the genetic disease in the model mammal; step C of comparing the severity of the symptoms of the genetic disease in step B with that in a case to which the test compound is not administered; and step D of evaluating the test compound as a compound having the prophylactic or ameliorating effect of the present invention when the severity of the symptoms of the genetic disease in step B is lower than that in the case to which the test compound is not administered.

Also, whether or not a certain compound has the skipping-inducing or promoting effect according to the present invention can be confirmed by a method for determining a compound having the skipping-inducing or promoting effect according to the present invention, comprising, for example, the steps of: incorporating a DNA fragment (minigene) comprising the mutant exon and its flanking regions (exon regions or intron regions) into an appropriate expression vector for mammalian cells to prepare a recombinant vector; transfecting mammalian cells with the recombinant vector; culturing transformed cells obtained by the transfection (hereinafter, also referred to as "transformed cells according to the present invention") in contact with the test compound; isolating RNA from the cultured transformed cells and amplifying RNA corresponding to the minigene by RT-PCR; analyzing (e.g., electrophoresing or sequencing) the amplification product to confirm whether the skipping of the mutant exon has been induced and/or promoted; and evaluating the test compound as a compound having the skipping-inducing or promoting effect according to the present invention when the skipping of the mutant exon has been induced and/or promoted.

Furthermore, whether or not a certain compound has the truncated protein expression-inducing or enhancing effect can be confirmed by a method for determining a compound having the truncated protein expression-inducing or enhancing effect, comprising the steps of: culturing the transformed cells according to the present invention in contact with the test compound; analyzing proteins expressed in the cultured transformed cells to confirm whether the expression of the truncated protein has been induced and/or enhanced; and evaluating the test compound as a compound having the truncated protein expression-inducing or enhancing effect when the expression of the truncated protein has been induced and/or enhanced. The truncated protein can be detected, for example, on the basis of the absence of signals derived from a peptide encoded by the mutant exon and the presence of signals derived from peptides encoded by the other exons in Western blotting analysis using an antibody against the peptide encoded by the mutant exon and antibodies against the peptides encoded by the other exons. Whether or not the truncated protein is a functional truncated protein can be confirmed on the basis of, for example, an index in which symptoms of the genetic disease is ameliorated when the truncated protein is expressed in a model mammal of the genetic disease targeted by the present invention. In this context, the "functional truncated protein" according to the present invention refers to a truncated protein that is encoded by mature mRNA lacking at least one exon of the gene responsible for the genetic disease and still has, at least to some extent, the functions (particularly, functions related to the genetic disease) of the full-length protein encoded by the normal gene corresponding to the gene.

Also, whether or not a certain compound is a Clk inhibitory compound can be confirmed easily by a method comprising the steps of: assaying the phosphorylating activity of Clk in the presence of the test compound; comparing the value of phosphorylating activity obtained as a result of the assay with that obtained in the absence of the test compound; and evaluating the test compound as a Clk inhibitory compound when the value of phosphorylating activity of Clk in the presence of the test compound is lower than that in the absence of the test compound. The Clk can be obtained easily by: isolating the Clk gene from the desired mammal on the basis of public Clk sequence information; integrating the gene into an appropriate expression vector; allowing the gene to be expressed; and then isolating the expressed Clk. The phosphorylating activity of Clk can be assayed using, for example, an antibody specifically binding to a phosphorylated SR protein, a Clk substrate SR protein that has been phosphorylated. Examples of the mammal that serves as the origin of the Clk gene can preferably include, but not particularly limited to, humans, monkeys, mice, rats, hamsters, guinea pigs, cattle, pigs, horses, rabbits, sheep, goats, cats, and dogs, more preferably humans.

The type of the "mutation" in the genetic disease targeted by the present invention is not particularly limited as long as the genetic disease is capable of forming a functional truncated protein by skipping of the exon comprising the mutation. Examples thereof can include nonsense mutations, splicing abnormalities, and (out-of-frame) mutations that shift the reading frame of amino acids from that of the corresponding normal wild-type gene, preferably nonsense mutations and out-of-frame mutations, more preferably nonsense mutations and out-of-frame mutations that suppress exonic splicing enhancer activity in the gene responsible for the genetic disease and/or enhance exonic splicing silencer activity in the gene, particularly preferably nonsense mutations or out-of-frame mutations in which the skipping of the exon comprising each nonsense mutation or out-of-frame mutation is induced or promoted. Examples of the out-of-frame mutations can include mutations that are gene deletions, duplications, or inversions and cause the shift of the reading frame of amino acids from that of the corresponding normal wild-type gene.

Figure 7:
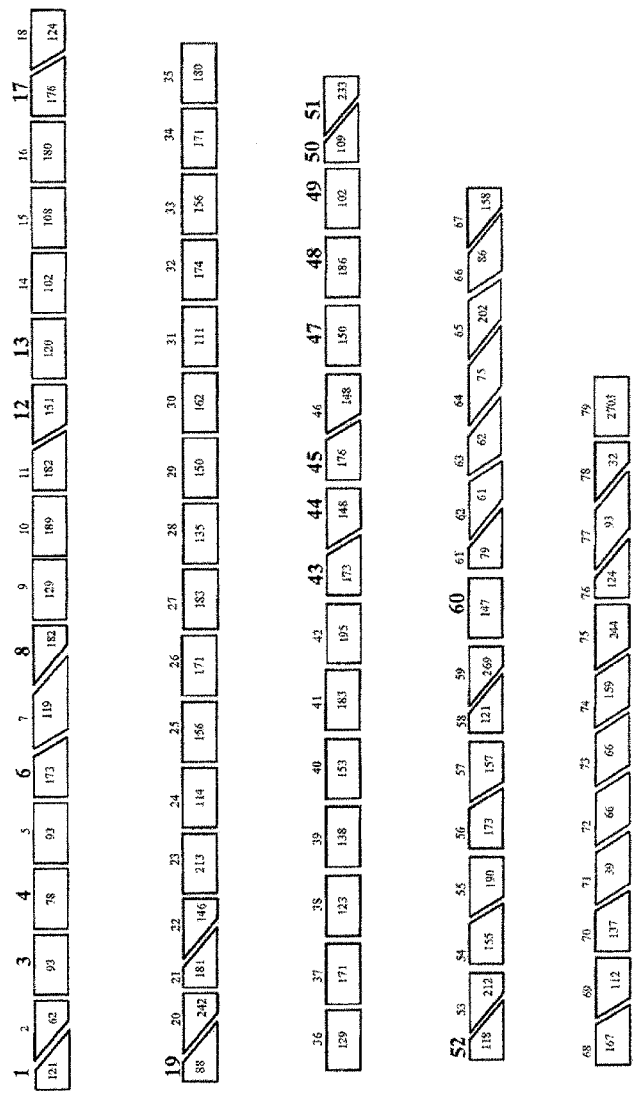
FIG. 7 is a diagram showing the arrangement of 79 exons in the human dystrophin gene. From this diagram, a base number corresponding to the boundary between exons in each codon can also be read.

In the present invention, the "exon comprising the mutation," which is to be skipped, is not limited to one exon comprising the mutation and may be several (preferably 2 to 8, more preferably 2 to 5, even more preferably 2 to 3, more preferably 2) adjacent exons including the exon of interest. The preferable number or range of the exon(s) can be selected appropriately by those skilled in the art on the basis of an index in which: remaining exons after skipping of the exon(s) are linked in-frame; or a truncated protein encoded by mature mRNA composed of the remaining exons becomes a functional truncated protein. In the case where the gene is, for example, the dystrophin gene, the number or range of exon(s) to be skipped can be determined on the basis of public exon information (FIG. 7). In this FIG. 7, the boundary between two exons indicated by the vertical line (see e.g., the line between exon 3 and exon 4) represents that the boundary between these exons agrees with the boundary between codons. The boundary between two exons indicated by the slightly angled oblique line (see e.g., the oblique line between exon 1 and exon 2) represents that the boundary between these exons is positioned between the first and second bases in a codon. The boundary between two exons indicated by the sharply angled oblique line (see e.g., the oblique line between exon 6 and exon 7) represents that the boundary between these exons is positioned between the second and third bases in a codon. Thus, for example, in the case of an out-of-frame mutation present in exon 51, exons 51 and 52 can be skipped or exons 50 and 51 can be skipped so that the remaining exons are in-frame. Alternatively, in the case of an out-of-frame mutation present in exon 53, exons 53 to 58 can be skipped or exons 52 and 53 can be skipped so that the remaining exons are in-frame.

The "exon skipping" or "skipping of the exon(s)" according to the present invention means that the exon(s) disappear, or are caused to disappear, from mRNA (mRNA precursor) formed by transcription from the gene during the processing of the mRNA precursor into mature mRNA.

The type of the genetic disease targeted by the present invention is not particularly limited as long as the genetic disease is caused by a mutation in an exon of a gene and is capable of forming a functional truncated protein by skipping of the exon comprising the mutation. Examples of the genetic disease can preferably include genetic diseases caused by a mutation in an exon of a gene, wherein some functional truncated proteins have been formed as a result of skipping of the exon comprising the mutation. More specifically, examples thereof can more preferably include the genetic disease whose causative gene is the dystrophin gene, wherein the functional truncated protein is functional truncated dystrophin, i.e., Duchenne muscular dystrophy. Examples of the Duchenne muscular dystrophy can more preferably include Duchenne muscular dystrophy, wherein the exon of the dystrophin gene is exon 31 or exon 27 of the dystrophin gene, particularly preferably Duchenne muscular dystrophy, wherein the mutation in exon 31 of the dystrophin gene is a nonsense mutation of guanine to thymine at nucleotide No. 4303 in a polynucleotide sequence of SEQ ID NO: 1 (dystrophin cDNA sequence) or the mutation in exon 27 of the dystrophin gene is an out-of-frame mutation that deletes guanine at nucleotide No. 3613 in the polynucleotide sequence of SEQ ID NO: 1.

Examples of the mammal recipient of the prophylactic or ameliorating agent of the present invention can preferably include, but not particularly limited to, humans, monkeys, mice, rats, hamsters, guinea pigs, cattle, pigs, horses, rabbits, sheep, goats, cats, and dogs, more preferably humans. In the case of using a Clk inhibitory compound in the prophylactic or ameliorating agent of the present invention, preferably, the origin of Clk on which the Clk inhibitory compound exerts its inhibitory effect agrees with the type of the mammal recipient of the prophylactic or ameliorating agent of the present invention, because the mammal can more benefit from the prophylactic or ameliorating effect of the present invention.

Examples of the preferable degree of the skipping-inducing or promoting effect according to the present invention possessed by the compound according to the present invention can preferably include an exon skip/inclusion ratio increased by 2 times or more, preferably 3 times or more, more preferably 4 times or more, even more preferably 5 times or more compared with that in the absence of the compound according to the present invention, wherein the exon skip/inclusion ratio is calculated by the steps of: culturing the transformed cells according to the present invention in contact with the compound according to the present invention (30 µM); isolating RNA from the cultured transformed cells and amplifying RNA corresponding to the minigene by RT-PCR; and analyzing (e.g., electrophoresing or sequencing) the amplification product to calculate the ratio of amplification products with the mutant exon skipped to amplification products without the skipped mutant exon. Examples of the particularly preferable degree of the skipping-inducing or promoting effect according to the present invention can include the effect of inducing the exon skip/inclusion ratio to a positive value larger than 0 when the exon skip/inclusion ratio in the absence of the compound according to the present invention is 0.

The prophylactic or ameliorating agent of the present invention may comprise optional components such as prophylactic or ameliorating agents for other genetic diseases, in addition to the compound according to the present invention, as long as the resulting prophylactic or ameliorating agent can produce the prophylactic or ameliorating effect of the present invention.

The compound according to the present invention contained in the prophylactic or ameliorating agent of the present invention can be formulated into an appropriate preparation according to a routine method. The dosage form of the preparation may be a solid preparation such as powders or granules and is preferably a liquid preparation such as solutions, emulsions, or suspensions, from the viewpoint of obtaining the more excellent prophylactic or ameliorating effect of the present invention. Examples of methods for producing the liquid preparation can preferably include methods involving mixing the compound according to the present invention with a solvent or further involving mixing the resulting mixture with a suspending agent or an emulsifying agent. Such a preparation of the compound according to the present invention can be supplemented with optional components such as appropriate pharmaceutically acceptable carriers, for example, excipients, binders, solvents, solubilizers, suspending agents, emulsifying agents, tonicity agents, buffers, stabilizers, soothing agents, preservatives, antioxidants, coloring agents, lubricants, disintegrants, wetting agents, adsorbents, sweetening agents, and diluents, according to pharmaceutical needs.

The amount of the compound according to the present invention contained in the prophylactic or ameliorating agent of the present invention is not particularly limited as long as the resulting prophylactic or ameliorating agent can produce the prophylactic or ameliorating effect of the present invention. Examples of the suitable amount can include 0.0001 to 99.9999% by mass, preferably 0.001 to 80% by mass, more preferably 0.001 to 50% by mass, even more preferably 0.005 to 20% by mass, with respect to the total amount of the prophylactic or ameliorating agent of the present invention.

The method for administering the prophylactic or ameliorating agent of the present invention is not particularly limited as long as the method can exert the prophylactic or ameliorating effect of the present invention. Examples thereof can include intravenous administration, oral administration, intramuscular administration, hypodermic administration, endermic administration, transnasal administration, and transpulmonary administration. The dose of the prophylactic or ameliorating agent of the present invention can be adjusted appropriately according to the severity of the genetic disease in a recipient, the body weight of the recipient, etc. Examples thereof can preferably include 0.1 µg to 10000 mg, more preferably 1 µg to 3000 mg, even more preferably 10 µg to 1000 mg of the compound according to the present invention per day in one adult.

The prophylactic or ameliorating agent of the present invention containing the compound according to the present invention can also be used as an exon skipping-inducing or promoting agent that induces or promotes the skipping of an exon in a gene comprising a mutation responsible for a genetic disease. Other aspects of the present invention provide, for example: use of the compound according to the present invention in the production of the prophylactic or ameliorating agent of the present invention; a method for using the compound according to the present invention in the prophylactic or ameliorating agent of the present invention; use of the compound according to the present invention for inducing or enhancing the expression of a functional truncated protein by skipping of an exon of a gene comprising a mutation responsible for a genetic disease; use of the compound of the present invention for preventing or ameliorating the genetic disease targeted by the present invention; a method for preventing or ameliorating the genetic disease targeted by the present invention, comprising administering the prophylactic or ameliorating agent of the present invention to a subject; and a method for inducing or promoting skipping of an exon of a gene comprising a mutation responsible for a genetic disease, comprising administering the exon skipping-inducing or promoting agent according to the present invention to a subject. The contents of terms in these uses or methods or preferable aspects thereof are as described above.

Hereinafter, the present invention will be described in detail with reference to Examples. However, the present invention is not intended to be limited to these Examples.

EXAMPLE 1

Mutation Analysis of Dystrophin Gene in Muscular Dystrophy Patient

More than 400 muscular dystrophy patients were analyzed for mutations in their dystrophin genes by a method shown below.
(Mutation Analysis)
DNA was isolated from the blood sample of each patient by the standard phenol-chloroform extraction method. Total RNA was isolated from peripheral lymphocytes collected from whole blood using the Ficoll-Paque density gradient method (manufactured by Amersham Biosciences AB) or isolated from a muscle section obtained by the slicing of a frozen muscle sample. Dystrophin mRNA expressed in skeletal muscle was analyzed by reverse-transcription PCR(RT-PCR) and RT-nested PCR. A region comprising exons 27 to 32 of the skeletal muscle-derived dystrophin mRNA was amplified using an internal primer set (forward c27f: CCTGTAGCACAAGAGGCCTTA (SEQ ID NO: 2) and reverse 2F: TCCACACTCTTTGTTTCCAATG (SEQ ID NO: 3)). This amplification product was purified and sequenced either directly or after subcloning into a pT7Blue-T vector (manufactured by Merck KGaA (Novagen)). This sequencing employed an automatic DNA sequencer (model 310; manufactured by Applied Biosystems, Inc.).

The case of one (patient No. KUCG797) of the analyzed muscular dystrophy patients was as follows: this patient, a 5-year-old boy, was born to healthy Japanese parents with no family history of muscle diseases. He started walking on his own at the age of 1 year and 4 months and had normal motor development. However, he exhibited a serum creatine kinase (CK) level of 2567 IU/l (normal level: less than 169 IU/l) in regular blood testing at the age of 2 years and was thus hospitalized. He underwent a diagnosis at the Kobe University Hospital and examined for a mutation in the dystrophin gene. Although the CK level then continued to rise gradually (1331 to 4740 IU/l), neither muscle weakness nor gait abnormality was observed. The boy underwent muscle biopsy when he was 5 years old. This study was carried out after getting the approval of the ethics committee of the Kobe University.

A point mutation was observed in exon 31 of the dystrophin gene of the patient KUCG797. This mutation replaced G by T at nucleotide No. 4303 in dystrophin cDNA (G by U in RNA) (c.4303G>T: FIG. 1a). Since this alteration of the nucleotide resulted in the replacement of a GAG codon encoding glutamic acid by a stop codon TAG (p.Glu1435X), this case was presumed to have grave DMD without producing dystrophin according to the reading frame rule described in Background Art.
(Skeletal Muscle Biopsy and Dystrophin Immunostaining)
Next, the patient (5 years old) was subjected to skeletal muscle biopsy and subsequent dystrophin immunostaining by a method shown below.

The rectus femoris muscle of KUCG797 was biopsied to obtain a skeletal muscle sample. This skeletal muscle sample was rapidly frozen using isopentane cold in liquid nitrogen. Serial frozen sections each having a thickness of 10 µm were prepared from the frozen skeletal muscle sample and analyzed by immunohistochemical staining. Specifically, the serial frozen sections each having a thickness of 10 µm were placed for 5 minutes in cold acetone and fixed. The resulting sections were blocked with normal goat serum and incubated overnight at 4° C. in the presence of anti-dystrophin antibodies (primary antibodies). The anti-dystrophin antibodies used were three types: DYS2 (manufactured by Novocastra Laboratories Ltd.), DYS3 (manufactured by Novocastra Laboratories Ltd.), and MANDYS1 (donated by Professor (Dr.) Glenn E. Morris). DYS2 recognizes a C-terminal epitope corresponding to exons 77 to 79 of the dystrophin gene. DYS3 recognizes an N-terminal epitope corresponding to exons 10 to 12 of the dystrophin gene. MANDYS1 recognizes an epitope (rod domain) corresponding to exons 31 and 32 of the dystrophin gene. The sections thus incubated were washed six times with PBS and then incubated at room temperature for 90 minutes in the presence of goat anti-mouse antibodies or goat anti-rabbit antibodies labeled with Alexa Fluor 488 as secondary antibodies. The resulting sections were washed and then observed under a fluorescence microscope. The results are shown in FIG. 1b. Panel e of FIG. 1b shows the results of staining with DYS2. Panel f of FIG. 1b shows the results of staining with DYS3. Panel g of FIG. 1b shows the results of staining with MANDYS1.

From the genotype of the dystrophin gene in KUCG797, this patient was presumed to have grave DMD. Against this presumption, the results of immunohistochemical staining showed sparse, discontinuous signals derived from the antibodies recognizing the N-terminal or C-terminal dystrophin domain, as in BMD (panel e or f in FIG. 1b). No signal was observed for the antibody MANDYS1 recognizing the domain corresponding to exon 31 and 32 of the dystrophin gene (panel g in FIG. 1b). A healthy person-derived skeletal muscle sample was immunohistologically stained as a positive control in the same way. As a result, signals were confirmed for all of the antibodies DYS2, DYS3, and MANDYS1 (panels b, c, and d in FIG. 1b).

(Analysis of RT-PCR Amplification Product)

In order to explain this contradiction between the genotype (DMD type) of the dystrophin gene in KUCG797 and the immunostaining pattern thereof, the present inventors hypothesized that the nonsense mutation in exon 31 of the dystrophin gene disrupted an exonic splicing enhancer (ESE) and brought about the skipping of the mutant exon (exon comprising the mutation). In order to demonstrate the possibility of this hypothesis, the skeletal muscle dystrophin mRNA of KUCG797 was analyzed by the RT-PCR amplification method.

Specifically, the region from exons 27 to 32 was amplified using total RNA isolated from KUCG797 as a template and the primers forward c27f and reverse 2F. The obtained amplification product was electrophoresed on 2% agarose gel in a tris-borate/EDTA buffer solution. The results are shown in FIG. 1c. The rightmost lane (Patient) shows the results obtained using KUCG797-derived total RNA as a template. The central lane (Control) shows the results obtained using healthy person-derived total RNA as a template. Only one type of amplification product was obtained from the region from exons 27 to 32 in the control, whereas, surprisingly, two types of amplification products were obtained in substantially the same amounts for KUCG797. One of these two types of amplification products had a size as predicted, and the other amplification product was smaller in size (FIG. 1c). As a result of sequencing this amplification product of the smaller size, skipped exon 31 was confirmed (FIG. 1d). On the one hand, results of sequencing the amplification product of the predicted size showed the sequences of exons 27 to 32 (793 nt) including the stop codon TAG in exon 31. On the other hand, the amplification product of the smaller size completely lacked the sequence of exon 31, but still had the intact sequences of the other exons (682 nt), suggesting that mutant exon 31 was skipped (FIG. 1c). Other introns of the KUCG797 dystrophin gene were examined for their splicing and consequently all confirmed to be normally spliced (data not shown). The dystrophin mRNA (682 nt) lacking exon 31 (111 nt) is in-frame and yields still-functional, albeit truncated, dystrophin (truncated dystrophin). Since the immunostaining described above employed the antibodies recognizing the N-terminal or C-terminal dystrophin domain, the truncated dystrophin was supposed to be stained. Thus, immunostaining was performed using the monoclonal antibody MANDYS1 against the region including exon 31. As a result, MANDYS1 did not recognize the truncated dystrophin (panel g in FIG. 1b).

These results demonstrated that the patient having the c.4303G>T (p.Glu1435X) point mutation in his dystrophin gene expressed two types of dystrophin mRNAs: full-length mRNA and an exon 31 deletion (Δexon 31) mutant. These results also suggested that this point mutation disrupted not only ORF of the dystrophin gene but also the splice signal of exon 31.

(Cell-Based Analysis of Splicing Using Minigene -1-)

In order to further analyze this hypothesis, a dystrophin gene fragment (mutant minigene) comprising mutant exon 31 and both its flanking introns was inserted to an H492 vector for cell-based analysis of splicing (Mol Genet Metab (2005) 85, 213-219; J Med Genet (2006) 43, 924-930; and Hum Genet (2007) 120, 737-742) to construct a plasmid (H492-dys Ex31 plasmid). The mRNA of this gene fragment was examined using Hela cells transfected with the plasmid. In this context, the H492 vector encodes two cassette exons (A and B) and intron sequences including a multicloning site.

The H492-dys Ex31 plasmid was constructed by the following method: the dystrophin gene fragment comprising mutant exon 31 and both its flanking intron regions was amplified by PCR from the genomic DNA of KUCG797. The primers used were intron 30f-NheI (GCGGCTAGCGT-GATCCACCTGCCTCGAC: SEQ ID NO: 4) and intron 31r-BamHI (GCGGGATCCTCAAATCCAATCTTGCCAAT: SEQ ID NO: 5). The obtained amplification product was digested with NheI and BamHI (manufactured by New England Biolabs Inc.), and the resulting fragment was inserted to H492 digested with both the enzymes. In this way, a plasmid (H492-dys Ex31m plasmid) comprising the KUCG797-derived fragment (mutant minigene) comprising mutant exon 31 and both its flanking intron regions was constructed (FIG. 1e). Also, the genomic DNA of a healthy person was used in the same way to construct a plasmid (H492-dys Ex31w plasmid) comprising a dystrophin gene fragment (wild-type minigene) comprising wild-type exon 31 and both its flanking intron regions (FIG. 1e). As a result of determining the whole sequences of the H492-dys Ex31m plasmid and the H492-dys Ex31w plasmid, these plasmids were both confirmed to comprise the fragment of interest.

Hela cells were transfected with the H492-dys Ex31m plasmid and the H492-dys Ex31w plasmid to obtain H492-dys Ex31 m/Hela and H492-dys Ex31w/Hela, respectively. This transfection was performed using Lipofectamine 2000 (manufactured by Invitrogen Corp.) according to the manual of the manufacturer. An mRNA precursor was transcribed from the CMV promoter (CMVp) in these cells obtained by the transfection.

A region comprising the minigene was amplified by RT-PCR using total RNA isolated from H492-dys Ex31 m/Hela or H492-dys Ex31w/Hela as a template and the primers intron 30f and intron 30r. The obtained amplification product was electrophoresed on 2% agarose gel in a tris-borate/EDTA buffer solution. The results are shown in FIG. 1f. The third left lane (m) shows the results obtained using H492-dys Ex31 m/Hela-derived total RNA as a template. The second left lane (w) shows the results obtained using H492-dys Ex31w/Hela-derived total RNA as a template. One RT-PCR product comprising exons A, 31, and B was observed in the transformed cell (H492-dys Ex31w/Hela) comprising the wild-type minigene. By contrast, two PCR products were detected in the transformed cell (H492-dys Ex31 m/Hela) comprising the mutant minigene (FIG. 1f). As a result of sequencing, the smaller DNA product was confirmed to comprise no exon 31 (data not shown). A negative control fragment was treated by RT-PCR in the same way except that reverse transcriptase (RT) was not added, and this RT-PCR product was electrophoresed on an agarose gel. The results are shown in the rightmost lane (m) and the second right lane (w) of FIG. 1f. These results demonstrated that the point mutation in this patient caused the skipping of dystrophin exon 31 and that some of the dystrophin genes cloned into H492 vectors have the ability to reproduce the exon 31 skipping observed in the patient muscle.

EXAMPLE 2

Analysis of Splicing Regulator Involved in Exon 31 Splicing

The results of Example 1 demonstrated that the point mutation in exon 31 of the KUCG797 dystrophin gene caused exon skipping. Thus, an attempt was made to identify a candidate factor regulating the skipping or inclusion of exon 31.
(Sequence Analysis Based on SpliceAid Program)

Figure 2:
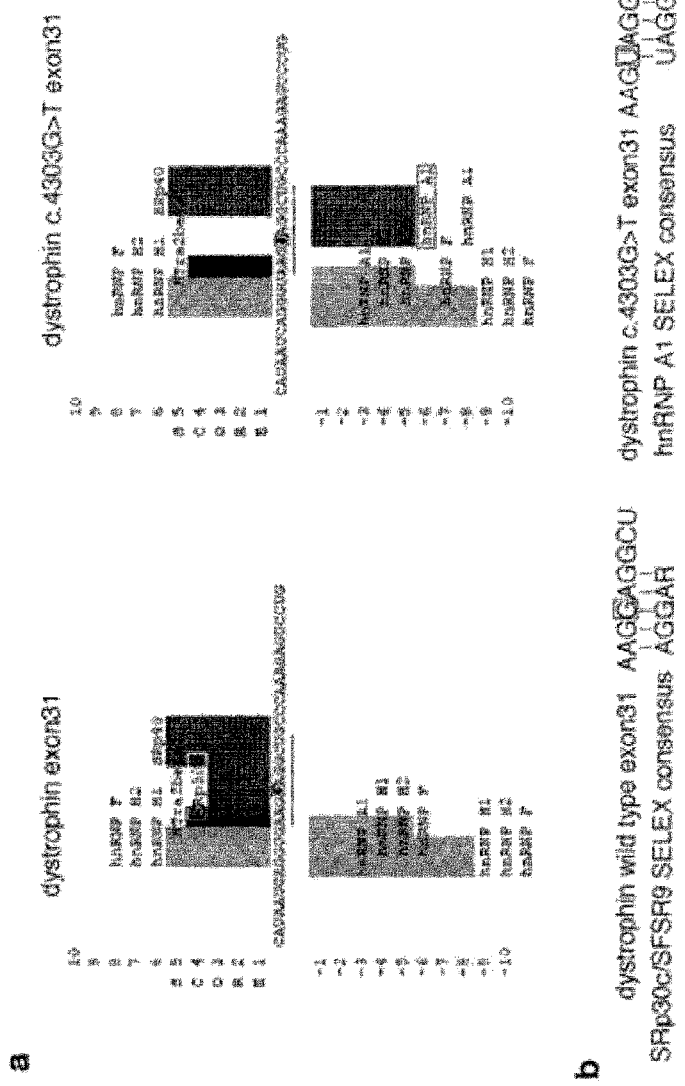
FIG. 2 is a diagram showing results of predicting a binding sequence in exon 31 to an RNA-binding protein that regulates splicing.

The RNA sequences of wild-type exon 31 and mutant exon 31 of the dystrophin gene were analyzed using the SpliceAid program (http://www.introni.it/splicing.html) (Bioinformatics (2009) 25, 1211-1213). As a result, the point mutation in this mutant exon 31 was shown to reduce binding strength to SRp30c/SRSF9 (SFSR9), a member of the SR protein family (FIG. 2a). The SR protein is known to bind to an exonic splicing enhancer (ESE), which is often rich in purine. The sequence of exon 31 is highly analogous to a high-affinity binding sequence for SRp30c/SRSF9 identified by SELEX (FIG. 2b) (RNA (2007) 13, 1287-1300). The mutation in mutant exon 31 not only disrupts the SRp30c/SRSF9-binding site but also causes a binding site with high affinity for hnRNP A1 (FIG. 2a). This means that the mutation in mutant exon 31 results in an RNA sequence highly homologous to the SELEX winner sequence for hnRNP A1 (FIG. 2b) (EMBO J. (1994) 13, 1197-1204). The hnRNP A1 protein is well known to bind to an exonic splicing silencer (ESS) to cause exon skipping. The results obtained using the SpliceAid program suggested that ESE in exon 31 of the dystrophin gene was recognized by SRp30c/SRSF9 and that this ESE was converted by the mutation to hnRNP A1-binding ESS.

(Gel Mobility Shift Assay)

In order to verify the hypothesis that ESE in exon 31 of the dystrophin gene was recognized by SRp30c/SRSF9 and that this ESE was converted by the mutation to hnRNP A1-binding ESS, binding activity against hnRNP A1 was first compared between mutant exon 31 RNA and wild-type exon 31 RNA by gel mobility shift assay. Specifically, this assay was conducted by a method shown below.

Human hnRNP A1 cDNA was amplified by PCR. The obtained amplified fragment was inserted to between the BamHI and NotI sites of GST-pcDNA3 to prepare a GST-hnRNP A1 plasmid. The whole sequence of this plasmid was determined to confirm the plasmid to comprise the fragment of interest. HEK293T cells were transfected with this GST-hnRNP A1 plasmid, and the obtained transformed cells were cultured. A whole cell lysate was prepared from the collected transformed cells according to the method described in the document (Methods Mol Biol (2008) 488, 357-365). The GST-hnRNP A1 protein was purified from the whole cell lysate using an anti-GST affinity resin (manufactured by Sigma-Aldrich Corp.), basically as described in the document (The Journal of Biological Chemistry (2002) 277, 7540-7545) except that the resin was washed twice with buffer solution E (20 mM Hepes-KOH (pH 7.9), 1000 mM KCl, 0.2 mM EDTA, 10% glycerol, and 1 mM DTT) before elution from the column. Subsequently, mutant exon 31 RNA or wild-type exon 31 RNA labeled with $^{32}$P was mixed with the GST-hnRNP A1 protein and incubated at 20° C. for 30 minutes. The obtained complex was subjected to gel mobility shift assay. Specifically, a method shown below was used.

The gel mobility shift assay was basically conducted according to the method described in the document (Nucleic Acids Research (1995) 23, 3638-3641). Specifically, each complex described above was assayed by electrophoresis on 8% natural polyacrylamide gel. Bands were analyzed by autoradiography. A binding buffer solution used in this assay contained 16 mM Hepes-KOH (pH 7.9), 80 mM KCl, 0.16 mM EDTA, 0.8 mM DTT, 8% glycerol, 100 ng/μl BSA, 50 ng/μl E. coli tRNA (manufactured by Sigma Chemical Co.), $5 \times 10^4$ cpm of RNA ($^{32}$P-labeled mutant exon 31 RNA or wild-type exon 31 RNA of the dystrophin gene), and 1 U/μl RNasin (registered trademark) (manufactured by Promega Corp.). The results of this gel mobility shift assay are shown in FIG. 3a.

Figure 3:
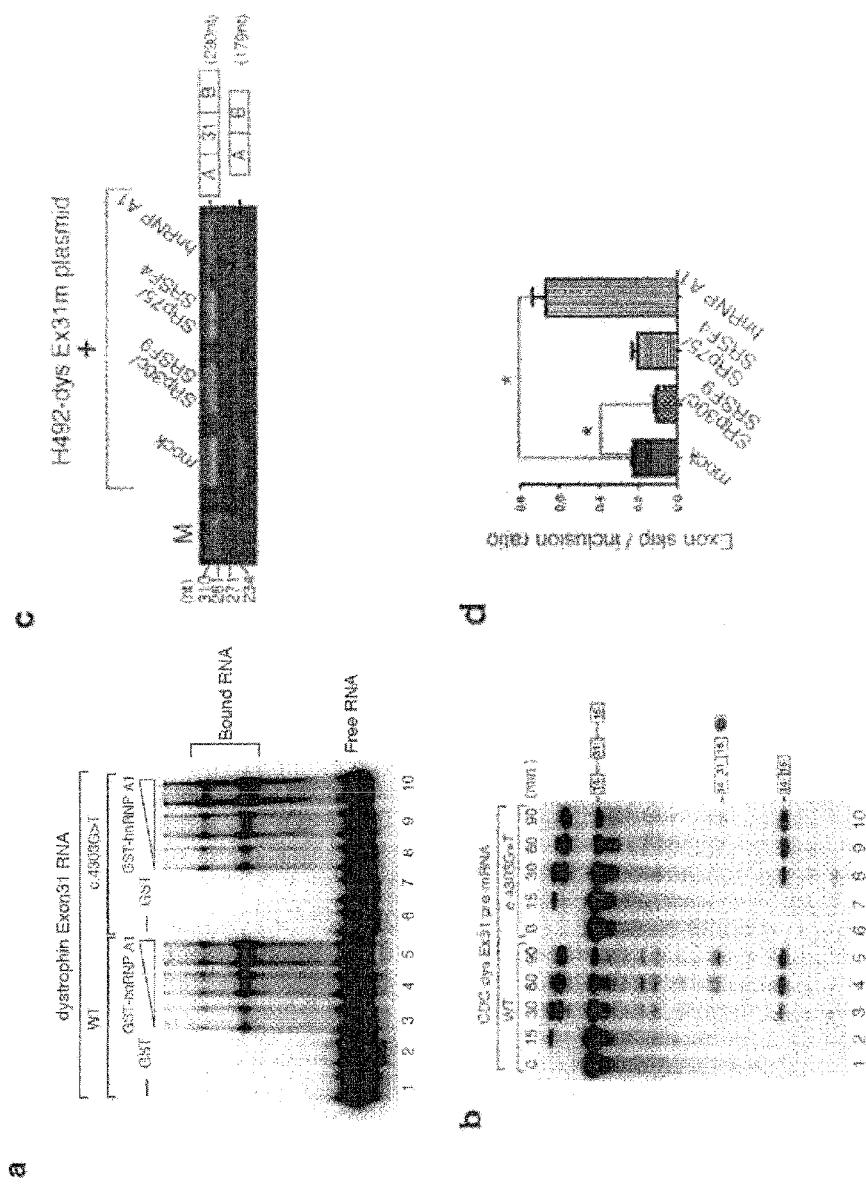
FIG. 3 is a diagram showing the manner in which the point mutation in dystrophin exon 31 found in a patient gene enhances binding to hnRNP A1 both in vitro and in vivo and enhances exon skipping.

As shown in FIG. 3a, a low concentration of hnRNP A1 bound to both wild-type exon 31 RNA and mutant exon 31 RNA at substantially the same levels (lanes 3 and 4 and lanes 8 and 9, respectively, in FIG. 3a). This probably indicates that the hnRNP A1-binding site common to both the wild type and the mutant is located on exon 31 (Hum Mol Genet (2006) 15, 999-1013). By contrast, a higher concentration of hnRNP A1 bound to mutant exon 31 RNA more efficiently than wild-type exon 31 RNA to form a larger complex including an hnRNP A1 multimer (lanes 5 and 10 in FIG. 3a). These results suggest that the point mutation in exon 31 found in the patient causes a new binding site with high affinity for hnRNP A1 on the exon 31 and consequently facilitates the distribution of a larger number of hnRNP A1 proteins on the mutant exon 31 RNA. The results described above strongly suggested the possibility that mutant exon 31 allowed to have stronger binding affinity for hnRNP A1 was not recognized efficiently as an exon during splicing. In order to examine this possibility, splicing assay was subsequently conducted in vitro.

(In Vitro Transcription and Splicing Assay)

In order to verify the suggested possibility that mutant exon 31 allowed to have stronger binding affinity for hnRNP A1 was not recognized efficiently as an exon during splicing, splicing assay was conducted in vitro.

First, an mRNA precursor comprising wild-type exon 31 or the mutant exon 31 of the dystrophin gene in the intron region of a chicken δ crystallin (CDC) mRNA precursor (Molecular Cell (2000) 6, 673-682) was prepared for this assay (see the construct on the right side of the panel in FIG. 3b). Specifically, wild-type exon 31 amplified by PCR was inserted to between the SacI and StyI sites of pCDC (Molecular Cell (2000) 6, 673-682) to prepare pCDC-dys Ex31w. Also, pCDC-dys Ex31m was prepared in the same way except that mutant exon 31 was used instead of wild-type exon 31. The pCDC-dys Ex31w plasmid and the pCDC-dys Ex31m plasmid were separately linearized with SmaI and used as templates in in vitro transcription. The in vitro transcription was performed according to the method described in the document (Molecular Cell (2000) 6, 673-682) so that the mRNA precursor was labeled with $^{32}$P. Subsequently, the transcribed mRNA precursor was purified. For in vitro splicing assay, 10 μl of the resulting mRNA precursor (CDC-dys Ex31w mRNA precursor or CDC-dys Ex31m mRNA precursor) was mixed with Hela nuclear extracts (manufactured by Cilbiotech be.) according to the method described in the document (Molecular cell (2000) 6, 673-682) and subsequently incubated at 30° C. for a time (0, 15, 30, 60, or 90 minutes) shown in the upper region of the panel. Each mRNA product obtained by the incubation was electrophoresed on 6% denaturing polyacrylamide gel. Subsequently, RNA bands were analyzed by autoradiography. The results are shown in FIG. 3b.

The results obtained using the CDC-dys Ex31w mRNA precursor comprising wild-type exon 31 (lanes 3 to 5 in FIG. 3b) were compared with the results obtained using the CDC-dys Ex31m mRNA precursor comprising mutant exon 31 (lanes 8 to 10 in FIG. 3b). As a result, the production efficiency of the mRNA product (mRNA product having a structure indicated by the filled circle on the right side of the panel in FIG. 3b) comprising exon 31 was lower in the latter than the former. By contrast, the exon 31-free mRNA product (mRNA product consisting of exons 14 and 15) was produced more efficiently using the CDC-dys Ex31m mRNA precursor comprising mutant exon 31.

(Cell-Based Analysis of Splicing Using Minigene -2-)

Next, the H492-dys Ex31 m/Hela cells prepared in Example 1 (Hela cells transfected with the plasmid comprising the mutant minigene) were further allowed to overexpress an RNA-binding protein (SRp30c/SRSF9 or SRp75/SRSF4) and examined for the influence of this overexpression on the splicing pattern of the mutant minigene.

A plasmid (Flag-SRp30c plasmid) used in SRp30c/SRSF9 overexpression was prepared by inserting PCR-amplified human SRp30c cDNA to between the BamHI and XhoI sites of Flag-pcDNA3 (The Journal of Biological Chemistry (2004) 279, 7009-7013). A plasmid (Flag-SRp75 plasmid) used in SRp75/SRSF4 overexpression was prepared by inserting PCR-amplified mouse SRp75 cDNA to between the BamHI and XhoI sites of Flag-pcDNA3.

In addition, a Flag-hnRNP A1 plasmid was prepared by the following method: human hnRNP A1 cDNA was amplified by PCR, and the obtained amplified fragment was inserted to between the BamHI and NotI sites of Flag-pcDNA3 (Nucleic Acids Research (2009) 37, 6515-6527) to prepare a Flag-hnRNP A1 plasmid. The whole sequence of this plasmid was determined to confirm the plasmid to comprise the fragment of interest. HEK293T cells were transfected with this Flag-hnRNP A1 plasmid, and the obtained transformed cells were cultured. A whole cell lysate was prepared from the collected transformed cells according to the method described in the document (Methods Mol Biol (2008) 488, 357-365). The Flag-hnRNP A1 protein was purified from the whole cell lysate using an anti-Flag-M2 affinity resin (manufactured by Sigma-Aldrich Corp.), basically as described in the document (The Journal of Biological Chemistry (2002) 277, 7540-7545) except that the resin was washed twice with buffer solution E (20 mM Hepes-KOH (pH 7.9), 1000 mM KCl, 0.2 mM EDTA, 10% glycerol, and 1 mM DTT) before elution from the column.

Hela cells were cotransfected with the H492-dys Ex31m plasmid and the Flag-SRp30c plasmid using Lipofectamine 2000 (manufactured by Invitrogen Corp.) to obtain H492-dys Ex31m.Flag-SRp30c/Hela. Also, Hela cells were cotransfected with the H492-dys Ex31m plasmid and the Flag-SRp75 plasmid using Lipofectamine 2000 (manufactured by Invitrogen Corp.) to obtain H492-dys Ex31m.Flag -SRp75/Hela. In addition, Hela cells were cotransfected with the H492-dys Ex31m plasmid and the Flag-hnRNP A1 using Lipofectamine 2000 (manufactured by Invitrogen Corp.) to obtain H492-dys Ex31m.Flag-hnRNP A1 plasmid/Hela.

Each of these transformed cells was subjected to splicing analysis in the same way as in the paragraph "Cell-based analysis of splicing using minigene -1-" of Example 1. The results are shown in FIG. 3c. The leftmost lane of FIG. 3c shows the results obtained using a marker. The second left lane (mock) shows the results obtained using H492-dys Ex31 m/Hela-derived total RNA as a template. The third left lane (SRp30c/SRSF9) shows the results obtained using H492-dys Ex31m.Flag -SRp30c/Hela-derived total RNA as a template. The second right lane (SRp75/SRSF4) shows the results obtained using H492-dys Ex31m.Flag-SRp75/Hela-derived total RNA as a template. The rightmost lane (hnRNP A) shows the results obtained using H492-dys Ex31m.Flag-hnRNP A1 plasmid/Hela-derived total RNA as a template. The band concentrations of FIG. 3c were determined to calculate the ratio of mRNA with exon 31 skipped to mRNA comprising exon 31 (exon skip/inclusion ratio). The results are shown in FIG. 3d.

As is evident from the results of FIGS. 3c and 3d, the exon skip/inclusion ratio significantly decreased for overexpressed SRp30c/SRSF9 (SRp30c/SRSF9 in FIGS. 3c and 3d) compared with the control (mock in FIGS. 3c and 3d). By contrast, the exon skip/inclusion ratio significantly rose for overexpressed hnRNP A1 (hnRNP A1 in FIGS. 3c and 3d) compared with the control (mock in FIGS. 3c and 3d). In the case of using the counterpart SRp75/SRSF4 (Molecular and Cellular Biology (1993) 13, 4023-4028), another member of the SR protein family (SRp75/SRSF4 in FIGS. 3c and 3d), the exon skip/inclusion ratio did not differ from the control (mock in FIGS. 3c and 3d), showing no change in splicing pattern.

These results strongly suggested that dystrophin exon 31 comprised SRp30c/SRSF9-dependent ESE and that the conversion of this ESE to hnRNP A1-binding ESS by mutation caused exon 31 skipping.

EXAMPLE 3

Effect of TG003 on Skipping of Mutant Exon 31 in H492-dys Ex31 m/Hela

The present inventors searched for various low-molecular-weight compounds in order to find a low-molecular-weight compound capable of promoting the skipping of exon 31 of the dystrophin gene. As a typical example thereof, results about TG003 and SRPIN340 will be described below.

Both TG003 and SRPIN340 are known as low-molecular-weight compounds that influence alternative splicing. SRPIN340 is a specific inhibitor for SR protein kinase (SRPK) (Proc Natl Acad Sci USA (2006) 103, 11329-11333) and can regulate alternative splicing, probably through the inhibition of the SRPK-mediated phosphorylation of the SR protein (Biochem J (2009) 417, 15-27; and Genome Biol (2009) 10, 242). The other compound designated as TG003 is a Clk kinase inhibitor. TG003 has also been shown to influence the alternative splicing of adenovirus E1A, SC35, and Clk itself (non-patent documents 12 and 13).

(Cell-Based Analysis of Splicing Using Minigene -3-)

Figure 4:
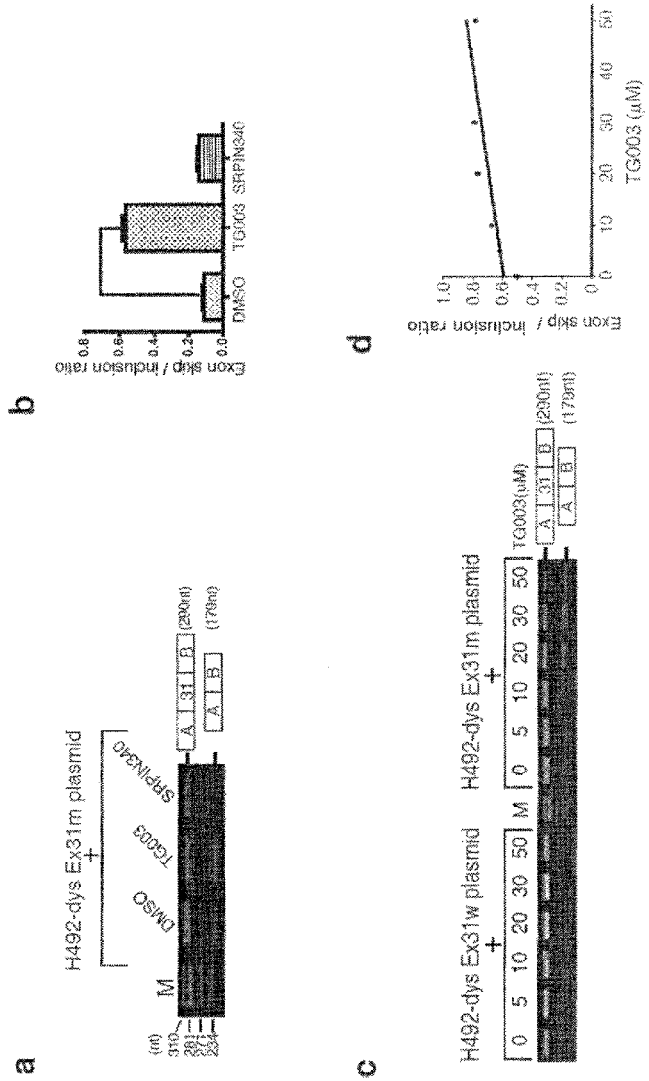
FIG. 4 is a diagram showing the manner in which TG003 promotes the skipping of mutant exon 31 in a dose-dependent manner in Hela cells.

H492-dys Ex31 m/Hela (Hela cells transfected with the plasmid comprising the mutant minigene) was incubated for 24 hours in a DMSO solution comprising 30 μM TG003 or a DMSO solution comprising 30 μM SRPIN340. A DMSO solution was used as a negative control and incubated in the same way. Each of the incubated cells was subjected to splicing analysis (RT-PCR analysis using total RNA extracted from cells) in the same way as in the paragraph "Cell-based analysis of splicing using minigene -1-" of Example 1. The results are shown in FIG. 4a. The leftmost lane of FIG. 4a shows the results obtained using a DNA size marker digested with ϕX174-HaeIII. The second left lane (DMSO) shows the results obtained using H492-dys Ex31 m/Hela treated with DMSO. The third left lane (TG003) shows the results obtained using H492-dys Ex31 m/Hela treated with TG003. The rightmost lane (SRPIN340) shows the results obtained using H492-dys Ex31 m/Hela treated with SRPIN340. The band concentrations of FIG. 4a were determined to calculate an exon skip/inclusion ratio. The results are shown in FIG. 4b.

As is evident from the results of FIGS. 4a and 4b, the cells treated with SRPIN340 (SRPIN340 in FIGS. 4a and 4b) exhibited the exon skip/inclusion ratio hardly different from that in the control (DMSO in FIGS. 4a and 4b), whereas the cells treated with TG003 (TG003 in FIGS. 4a and 4b) exhibited the exon skip/inclusion ratio significantly larger than that of the control (DMSO in FIGS. 4a and 4b). This demonstrated that SRPIN340 hardly influenced the skipping of exon 31, whereas TG003 significantly promoted the skipping of exon 31.

(Cell-Based Analysis of Splicing Using Minigene -4-)

From the results of "Cell-based analysis of splicing using minigene -3-," it was also possible that TG003 would promote not only the skipping of mutant exon 31 but also the skipping of wild-type exon 31. Thus, H492-dys Ex31 m/Hela (Hela cells transfected with the plasmid comprising the mutant minigene) as well as H492-dys Ex31w/Hela (Hela cells transfected with the plasmid comprising the wild-type minigene) was used in splicing analysis in the same way as in the paragraph "Cell-based analysis of splicing using minigene -3-." In this analysis, the solution used for cell treatment was a DMSO solution comprising varying concentrations (0 µM, 5 µM, 10 µM, 20 µM, 30 µM, and 50 µM) of TG003. The results are shown in FIG. 4c. The band densities of FIG. 4c were determined to calculate an exon skip/inclusion ratio. The results are shown in FIG. 4d.

As is evident from the results of FIGS. 4c and 4d, TG003 promoted the skipping of exon 31 in a dose-dependent manner in H492-dys Ex31 m/Hela (Hela cells transfected with the plasmid comprising the mutant minigene). By contrast, TG003 even at 50 µM did not cause the skipping of exon 31 in H492-dys Ex31w/Hela (Hela cells transfected with the plasmid comprising the wild-type minigene). As a result, the ratio was plotted substantially along the abscissa in the graph of FIG. 4d. These results demonstrated that TG003 specifically promoted the skipping of mutant exon 31 without promoting the skipping of wild-type exon 31.

EXAMPLE 4

Effect of TG003 on Skipping of Mutant Exon 27 in H492-Dys Ex27 m/Hela

In order to confirm whether or not TG003 also exerted a skipping-promoting effect on a mutation in an exon other than exon 31 in the dystrophin gene, a mutation in the dystrophin gene derived from a muscular dystrophy patient different from the patient KUCG797 was analyzed. The mutation in the dystrophin gene of this patient was found in exon 27. This mutation deleted guanine at nucleotide No. 3613 (c.3613delG) in the dystrophin cDNA (SEQ ID NO: 1). This mutation is an out-of-frame mutation that shifts the reading frame of the dystrophin cDNA (SEQ ID NO: 1), resulting in a stop codon (termination codon) in a region slightly closer to the C terminus than the mutation (region at nucleotide Nos. 3641 to 3643 in the dystrophin cDNA (SEQ ID NO: 1)). This case was presumed from the genotype to have grave DMD without producing dystrophin according to the reading frame rule described in Background Art in the present specification. However, the actual symptoms were milder than presumed.

A dystrophin gene fragment comprising mutant exon 27 and both its flanking intron regions was amplified by PCR from the genomic DNA of this patient. The primers used were intron 26f-NheI (GCGGCTAGCAAATTTATGGAAGAGACTGGAGTTCA: SEQ ID NO: 6) and intron 27r-BamHI (GCGGGATCCCAAGTTAAGCAAATGGCCCAAA: SEQ ID NO: 7). This amplification product was digested with NheI (manufactured by New England Biolabs Inc.) and BamHI (manufactured by New England Biolabs Inc.), and the resulting fragment was inserted to an H492 vector digested with both the enzymes. In this way, a plasmid (H492-dys Ex27m) comprising the patient-derived fragment comprising mutant exon 27 and both its flanking intron regions was constructed. Also, the genomic DNA of a healthy person was used in the same way to construct a plasmid (H492-dys Ex27w) comprising a dystrophin gene fragment comprising wild-type exon 27 and both its flanking intron regions. As a result of determining the whole sequences of the H492-dys Ex27m plasmid and the H492-dys Ex27w plasmid, these plasmids were both confirmed to comprise the fragment of interest.

Hela cells were transfected with H492-dys Ex27m and H492-dys Ex27w in the same way as in the paragraph "Cell-based analysis of splicing using minigene -1-" to obtain H492-dys Ex27 m/Hela and H492-dys Ex27 m/Hela, respectively.

Figure 5:
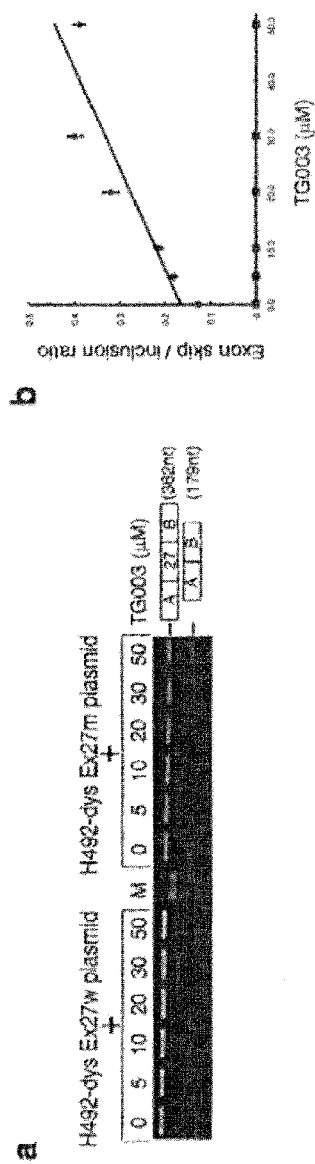
FIG. 5 is a diagram showing the manner in which TG003 promotes the skipping of mutant exon 27 in a dose-dependent manner in Hela cells.

Splicing analysis was conducted in the same way as in the paragraph "Cell-based analysis of splicing using minigene -4-" except that H492-dys Ex27 m/Hela and H492-dys Ex27 m/Hela were used instead of H492-dys Ex31 m/Hela and H492-dys Ex31 m/Hela, respectively. The results are shown in FIG. 5a. The band concentrations of FIG. 5a were determined to calculate an exon skip/inclusion ratio. The results are shown in FIG. 5b.

As is evident from the results of FIGS. 5a and 5b, TG003 promoted the skipping of exon 27 in a dose-dependent manner in H492-dys Ex27 m/Hela comprising mutant exon 27. By contrast, TG003 even at 50 µM did not cause the skipping of exon 27 in H492-dys Ex27w/Hela comprising wild-type exon 27. As a result, the ratio was plotted substantially along the abscissa in the graph of FIG. 5b. This demonstrated that TG003 specifically promoted the skipping of mutant exon 27 without promoting the skipping of wild-type exon 27. These results demonstrated that TG003 promoted not only the skipping of mutant exon 31 but also the skipping of mutant exon 27.

EXAMPLE 5

Effect of TG003 on Skipping of Mutant Exon 31 in KUCG797-Derived Cell

Next, the influence of TG003 on the splicing of the dystrophin gene was examined using patient (KUCG797)-derived muscle cells.

(Splicing Analysis in KUCG797-Derived Muscle Cell)

First, muscle cells collected from KUCG797 were primarily cultured. Specifically, this culture was performed by the following method: the patient-derived muscle cells were cultured in a Dulbecco's modified Eagle's medium (DMEM) (manufactured by Sigma-Aldrich Corp.) supplemented with 20% FBS (manufactured by Life Technologies Corp. (Gibco)), 4% Ultroser (registered trademark) G (manufactured by Pall Corp.), and 1% Antibiotic-Antimycotic (manufactured by Life Technologies Corp. (Gibco)) until confluent in a 6-well plate (Gelatin-Coated micro plate 6 well with Lid; manufactured by IWAKI). In order to differentiate the muscle cells into myotubes, the primary muscle cells were cultured for 2 weeks in the presence or absence of varying concentrations (1 µM, 2 µM, 5 µM, 7 µM, and 10 µM) of TG003 in a Dulbecco's modified Eagle's medium (DMEM) (manufactured by Sigma-Aldrich Corp.) supplemented with 2% horse serum (manufactured by Life Technologies (Gibco)) and 1% Antibiotic-Antimycotic (manufactured by Life Technologies Corp. (Gibco)). The medium and TG003 were replaced by fresh ones every 2 days.

These cultured muscle cells were used in splicing analysis. This splicing analysis employed the same method as in the paragraph "Cell-based analysis of splicing using minigene -3-" except that the primers forward c27f and reverse 2F were used instead of the primers intron 30f-NheI and intron 31r-BamHI, respectively. The primers forward c27f and reverse 2F are a primer set that amplifies the region from exons 27 to 32 of the dystrophin gene. The results of this splicing analysis are shown in FIG. 6a. The band concentrations of FIG. 6a were determined to calculate an exon skip/inclusion ratio. The results are shown in FIG. 6b.

As is evident from the results of FIGS. 6a and 6b, TG003 promoted the skipping of exon 31 in a dose-dependent manner even in the case of using the KUCG797-derived muscle cells. These results suggested that TG003 was capable of promoting the skipping of mutant exon 31 in patient-derived cells. Furthermore, TG003 was strongly expected to enhance the expression of truncated dystrophin that still had the original functions of dystrophin to some extent.

(Analysis of Truncated Dystrophin Expression in KUCG797-Derived Muscle Cell)

In order to confirm whether or not truncated dystrophin was actually expressed in the KUCG797-derived muscle cells, Western blotting analysis shown below was conducted.

The KUCG797-derived primary muscle cells were cultured for 2 weeks in the presence or absence of 7 μM TG003 in a Dulbecco's modified Eagle's medium (DMEM) (manufactured by Sigma-Aldrich Corp.) supplemented with 2% horse serum (manufactured by Life Technologies Corp. (Gibco)) and 1% Antibiotic-Antimycotic (manufactured by Life Technologies Corp. (Gibco)). The medium and TG003 were replaced by fresh ones every 2 days. These cultured muscle cells were washed twice with PBS and collected using 1× Cell Lysis Buffer (manufactured by Cell Signaling Technology, Inc.). Total proteins extracted from the collected cells were applied to a polyacrylamide gel (PAGEL, manufactured by ATTO Corp.) with 3 to 10% gradients. The amount of the total proteins applied was set to 4 μg for the control, 20 μg for the TG003 (0 μM)-untreated cells comprising the mutation, and 60 μg for the TG003 (7 μM)-treated cells comprising the mutation. The protein fractions electrophoresed on the polyacrylamide gel were transferred to HYBOND-P membrane (manufactured by GE Healthcare). The membrane was subjected to Western blotting analysis using ECL advance Western Blotting Detection kit (manufactured by GE Healthcare) according to the manual of the manufacturer. An antibody against the C terminus of dystrophin (NCL-DYS2, manufactured by Leica Biosystems) and an antibody against a region corresponding to dystrophin exon 31 (8H11, manufactured by Santa Cruz Biotechnology, Inc.) were used at dilution ratios of 1:10 and 1:100, respectively, in the incubation of the membrane. The immunocomplex of dystrophin and the anti-dystrophin antibody was detected using an anti-mouse IgG antibody (manufactured by GE Healthcare). Western blotting analysis of desmin was conducted according to the same protocol as above. An anti-desmin antibody (H-76, manufactured by Santa Cruz Biotechnology, Inc.) was used at a dilution ratio of 1:50. The immunocomplex of desmin and the anti-desmin antibody was detected using an anti-rabbit IgG antibody (manufactured by GE Healthcare).

Figure 6:
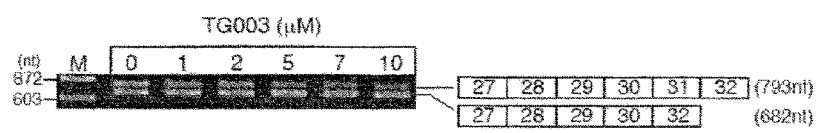
FIG. 6 is a diagram showing that TG003 promotes not only the skipping of mutant exon 31 but also the expression of truncated dystrophin (exon 31-deficient dystrophin) in patient-derived cells.
Figure 6:
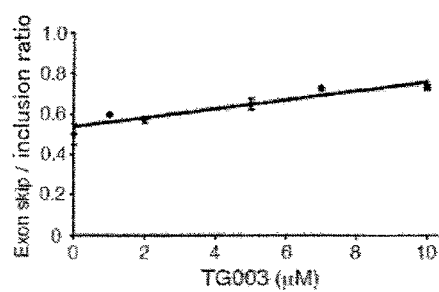
Figure 6:
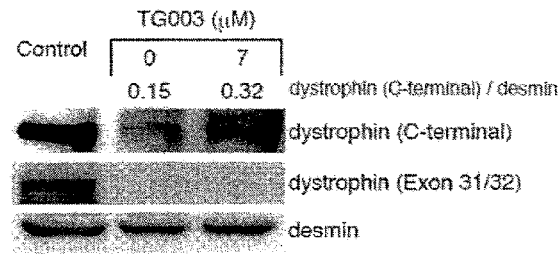

The results of the Western blotting analysis are shown in FIG. 6c. As is evident from the results obtained using the antibody against the C terminus of dystrophin (dystrophin (C-terminal)), the administration of TG003 was shown to enhance the expression of dystrophin. This dystrophin could not be detected using the antibody against a region corresponding to exon 31 (results indicated by dystrophin (Exon 31/32) in FIG. 6), indicating that this dystrophin lacked the region corresponding to exon 31 (peptide encoded by exon 31). These results demonstrated that TG003 promoted the exon 31 skipping in the KUCG797-derived cells having the c.4303G>T mutation to thereby promote the expression of truncated dystrophin.

INDUSTRIAL APPLICABILITY

The present invention can be used preferably in the field of prophylaxis or amelioration of a genetic disease. More specifically, the present invention can be used preferably in the field of prophylaxis or amelioration of a genetic disease that is caused by a mutation in an exon of a gene and is capable of forming a functional truncated protein by skipping of the exon comprising the mutation.

The invention claimed is:

1. An ameliorating method for a genetic disease that is caused by a mutation in an exon of a gene and is capable of forming a functional truncated protein by skipping of the exon comprising the mutation, comprising administering a Cdc-like kinase inhibitory compound having a molecular weight of 1500 or lower to a subject and represented by the following formula (1):

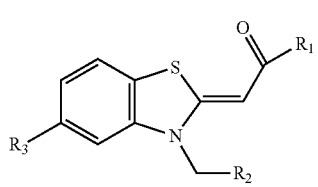

(1)

wherein R1 and R2 each independently represent a linear or branched $C_1$-$C_{10}$ hydrocarbon group; and R3 represents a methoxy group, an ethoxy group, an acetoxy group, or a halogen atom,
wherein the mutation in an exon of a gene is a nonsense mutation.

2. The ameliorating method according to claim 1, wherein the nonsense mutation suppresses exonic splicing enhancer activity in the gene and/or enhances exonic splicing silencer activity in the gene.

3. An ameliorating method for a genetic disease that is caused by a mutation in an exon of a gene and is capable of forming a functional truncated protein by skipping of the exon comprising the mutation, comprising administering a Cdc-like kinase inhibitory compound having a molecular weight of 1500 or lower to a subject and represented by the following formula (1):

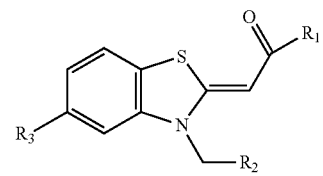

(1)

wherein R1 and R2 each independently represent a linear or branched $C_1$-$C_{10}$ hydrocarbon group; and R3 represents a methoxy group, an ethoxy group, an acetoxy group, or a halogen atom,
wherein the gene is dystrophin gene, the functional truncated protein is a functional truncated dystrophin protein, and the genetic disease is Duchenne muscular dystrophy.

4. The ameliorating method according to claim 3, wherein the exon of the dystrophin gene is exon 31 or exon 27 of the dystrophin gene.

5. The ameliorating method according to claim 4, wherein the mutation in exon 31 of the dystrophin gene is a nonsense mutation of guanine to thymine at nucleotide No: 4303 in the polynucleotide sequence of SEQ ID NO: 1, and the mutation in exon 27 is an out-of-frame mutation that deletes guanine at nucleotide No: 3613 in the polynucleotide sequence of SEQ ID NO: 1.

6. An ameliorating method for a genetic disease that is caused by a mutation in an exon of a gene and is capable of forming a functional truncated protein by skipping of the exon comprising the mutation, comprising administering a Cdc-like kinase inhibitory compound having a molecular weight of 1500 or lower to a subject and represented by the following formula (1):

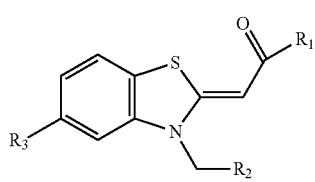

(1)

wherein R1 represents a methyl group, R2 represents a methyl group, and R3 represents a methoxy group,
wherein the mutation in an exon of a gene is a nonsense mutation.

7. The ameliorating method according to claim 6, wherein the nonsense mutation suppresses exonic splicing enhancer activity in the gene and/or enhances exonic splicing silencer activity in the gene.

8. The ameliorating method according to claim 7, wherein the gene is dystrophin gene, the functional truncated protein is a functional truncated dystrophin protein, and the genetic disease is Duchenne muscular dystrophy.

9. The ameliorating method according to claim 8, wherein the exon of the dystrophin gene is exon 31 or exon 27 of the dystrophin gene.

10. The ameliorating method according to claim 9, wherein the mutation in exon 31 of the dystrophin gene is a nonsense mutation of guanine to thymine at nucleotide No: 4303 in the polynucleotide sequence of SEQ ID NO: 1, and the mutation in exon 27 is an out-of-frame mutation that deletes guanine at nucleotide No: 3613 in the polynucleotide sequence of SEQ ID NO: 1.

* * * * *

SEQUENCE LISTING

<160> NUMBER OF SEQ ID NOS: 7

<210> SEQ ID NO 1
<211> LENGTH: 13749
<212> TYPE: DNA
<213> ORGANISM: Homo sapiens
<220> FEATURE:
<223> OTHER INFORMATION: dystrophin cDNA
<220> FEATURE:
<223> OTHER INFORMATION: Inventor:Hagiwara, Masatoshi; Kataoka, Naoyuki
      Inventor:Matsuo, Masafumi; Nishida, Atsushi

<400> SEQUENCE: 1

```
atgctttggt gggaagaagt agaggactgt tatgaaagag aagatgttca aaagaaaaca      60
ttcacaaaat gggtaaatgc acaattttct aagtttggga agcagcatat tgagaacctc     120
ttcagtgacc tacaggatgg gaggcgcctc ctagacctcc tcgaaggcct gacagggcaa     180
aaactgccaa aagaaaaagg atccacaaga gttcatgccc tgaacaatgt caacaaggca     240
ctgcgggttt tgcagaacaa taatgttgat ttagtgaata ttggaagtac tgacatcgta     300
gatggaaatc ataaactgac tcttggtttg atttggaata taatcctcca ctggcaggtc     360
aaaaatgtaa tgaaaatat catggctgga ttgcaacaaa ccaacagtga aaagattctc     420
ctgagctggg tccgacaatc aactcgtaat tatccacagg ttaatgtaat caacttcacc     480
```

```
accagctggt ctgatggcct ggctttgaat gctctcatcc atagtcatag gccagaccta      540
tttgactgga atagtgtggt ttgccagcag tcagccacac aacgactgga acatgcattc      600
aacatcgcca gatatcaatt aggcatagag aaactactcg atcctgaaga tgttgatacc      660
acctatccag ataagaagtc catcttaatg tacatcacat cactcttcca agttttgcct      720
caacaagtga gcattgaagc catccaggaa gtggaaatgt tgccaaggcc acctaaagtg      780
actaaagaag aacattttca gttacatcat caaatgcact attctcaaca gatcacggtc      840
agtctagcac agggatatga gagaacttct tcccctaagc ctcgattcaa gagctatgcc      900
tacacacagg ctgcttatgt caccacctct gaccctacac ggagcccatt tccttcacag      960
catttggaag ctcctgaaga caagtcattt ggcagttcat tgatggagag tgaagtaaac     1020
ctggaccgtt atcaaacagc tttagaagaa gtattatcgt ggcttctttc tgctgaggac     1080
acattgcaag cacaaggaga gatttctaat gatgtggaag tggtgaaaga ccagtttcat     1140
actcatgagg ggtacatgat ggatttgaca gcccatcagg gccgggttgg taatattcta     1200
caattgggaa gtaagctgat tggaacagga aaattatcag aagatgaaga aactgaagta     1260
caagagcaga tgaatctcct aaattcaaga tgggaatgcc tcagggtagc tagcatggaa     1320
aaacaaagca atttacatag agttttaatg gatctccaga atcagaaact gaaagagttg     1380
aatgactggc taacaaaaac agaagaaaga acaaggaaaa tggaggaaga gcctcttgga     1440
cctgatcttg aagacctaaa acgccaagta caacaacata aggtgcttca agaagatcta     1500
gaacaagaac aagtcagggt caattctctc actcacatgg tggtggtagt tgatgaatct     1560
agtggagatc acgcaactgc tgctttggaa gaacaactta aggtattggg agatcgatgg     1620
gcaaacatct gtagatggac agaagaccgc tgggttcttt tacaagacat ccttctcaaa     1680
tggcaacgtc ttactgaaga acagtgcctt tttagtgcat ggctttcaga aaagaagat      1740 gcagtgaaca agattcacac aactggcttt aaagatcaaa atgaaatgtt atcaagtctt     1800
caaaaactgg ccgttttaaa agcggatcta gaaaagaaaa agcaatccat gggcaaactg     1860
tattcactca aacaagatct tctttcaaca ctgaagaata agtcagtgac ccagaagacg     1920
gaagcatggc tggataactt tgcccggtgt tgggataatt tagtccaaaa acttgaaaag     1980
agtacagcac agatttcaca ggctgtcacc accactcagc catcactaac acagacaact     2040
gtaatggaaa cagtaactac ggtgaccaca agggaacaga tcctggtaaa gcatgctcaa     2100
gaggaacttc caccaccacc tccccaaaag aagaggcaga ttactgtgga ttctgaaatt     2160
aggaaaaggt tggatgttga tataactgaa cttcacagct ggattactcg ctcagaagct     2220
gtgttgcaga gtcctgaatt tgcaatcttt cggaaggaag gcaacttctc agacttaaaa     2280 gaaaagtca atgccataga gcgagaaaaa gctgagaagt tcagaaaact gcaagatgcc     2340
agcagatcag ctcaggccct ggtggaacag atggtgaatg agggtgttaa tgcagatagc     2400
atcaaacaag cctcagaaca actgaacagc cggtggatcg aattctgcca gttgctaagt     2460
gagagactta actggctgga gtatcagaac aacatcatcg ctttctataa tcagctacaa     2520
caattggagc agatgacaac tactgctgaa aactggttga aaatccaacc caccaccca      2580 tcagagccaa cagcaattaa aagtcagtta aaaatttgta aggatgaagt caaccggcta     2640
tcaggtcttc aacctcaaat tgaacgatta aaaattcaaa gcatagccct gaaagagaaa     2700
ggacaaggac ccatgttcct ggatgcagac tttgtggcct ttacaaatca ttttaagcaa     2760 gtctttttctg atgtgcaggc cagagagaaa gagctacaga caattttga cacttttgcca     2820 ccaatgcgct atcaggagac catgagtgcc atcaggacat gggtccagca gtcagaaacc     2880
```

```
aaactctcca tacctcaact tagtgtcacc gactatgaaa tcatggagca gagactcggg    2940
gaattgcagg ctttacaaag ttctctgcaa gagcaacaaa gtggcctata ctatctcagc    3000
accactgtga aagagatgtc gaagaaagcg ccctctgaaa ttagccggaa atatcaatca    3060
gaatttgaag aaattgaggg acgctggaag aagctctcct cccagctggt tgagcattgt    3120
caaaagctag aggagcaaat gaataaactc cgaaaaattc agaatcacat acaaaccctg    3180
aagaaatgga tggctgaagt tgatgttttt ctgaaggagg aatggcctgc ccttggggat    3240
tcagaaattc taaaaaagca gctgaaacag tgcagacttt tagtcagtga tattcagaca    3300
attcagccca gtctaaacag tgtcaatgaa ggtgggcaga agataaagaa tgaagcagag    3360
ccagagtttg cttcgagact tgagacagaa ctcaaagaac ttaacactca gtgggatcac    3420
atgtgccaac aggtctatgc cagaaaggag gccttgaagg gaggtttgga gaaaactgta    3480
agcctccaga aagatctatc agagatgcac gaatggatga cacaagctga agaagagtat    3540
cttgagagag attttgaata taaaactcca gatgaattac agaaagcagt tgaagagatg    3600
aagagagcta agaagaggc ccaacaaaaa gaagcgaaag tgaaactcct tactgagtct    3660
gtaaatagtg tcatagctca agctccacct gtagcacaag aggccttaaa aaaggaactt    3720
gaaactctaa ccaccaacta ccagtggctc tgcactaggc tgaatgggaa atgcaagact    3780
ttggaagaag tttgggcatg ttggcatgag ttattgtcat acttggagaa agcaaacaag    3840
tggctaaatg aagtagaatt taaacttaaa accactgaaa acattcctgg cggagctgag    3900
gaaatctctg aggtgctaga ttcacttgaa aatttgatgc acattcaga ggataaccca    3960 aatcagattc gcatattggc acagacccta acagatggcg gagtcatgga tgagctaatc    4020
aatgaggaac ttgagacatt taattctcgt tggagggaac tacatgaaga ggctgtaagg    4080
aggcaaaagt tgcttgaaca gagcatccag tctgcccagg agactgaaaa atccttacac    4140
ttaatccagg agtccctcac attcattgac aagcagttgg cagcttatat tgcagacaag    4200
gtggacgcag ctcaaatgcc tcaggaagcc cagaaaatcc aatctgattt gacaagtcat    4260
gagatcagtt tagaagaaat gaagaaacat aatcagggga aggaggctgc ccaaagagtc    4320
ctgtctcaga ttgatgttgc acagaaaaaa ttacaagatg tctccatgaa gtttcgatta    4380
ttccagaaac cagccaattt tgagcagcgt ctacaagaaa gtaagatgat tttagatgaa    4440
gtgaagatgc acttgcctgc attggaaaca agagtgtgg aacaggaagt agtacagtca    4500
cagctaaatc attgtgtgaa cttgtataaa agtctgagtg aagtgaagtc tgaagtggaa    4560
atggtgataa agactggacg tcagattgta cagaaaaagc agacggaaaa tcccaaagaa    4620
cttgatgaaa gagtaacagc tttgaaattg cattataatg agctgggagc aaaggtaaca    4680
gaaagaaagc aacagttgga gaaatgcttg aaattgtccc gtaagatgcg aaaggaaatg    4740
aatgtcttga cagaatggct ggcagctaca gatatggaat tgacaaagag atcagcagtt    4800
gaaggaatgc ctagtaattt ggattctgaa gttgctggg gaaaggctac tcaaaaagag    4860
attgagaaac agaaggtgca cctgaagagt atcacagagg taggagaggc cttgaaaaca    4920
gttttgggca agaaggagac gttggtggaa gataaactca gtcttctgaa tagtaactgg    4980
ataGCTgtca cctcccgagc agaagagtgg ttaaatcttt tgttggaata ccagaaacac    5040
atggaaactt ttgaccagaa tgtggaccac atcacaaagt ggatcattca ggctgacaca    5100
cttttggatg aatcagagaa aaagaaaccc cagcaaaaag aagacgtgct taagcgttta    5160
aaggcagaac tgaatgacat acgcccaaag gtggactcta cacgtgacca agcagcaaac    5220
```

```
ttgatggcaa accgcggtga ccactgcagg aaattagtag agccccaaat ctcagagctc    5280
aaccatcgat ttgcagccat ttcacacaga attaagactg gaaaggcctc cattcctttg    5340
aaggaattgg agcagtttaa ctcagatata caaaaattgc ttgaaccact ggaggctgaa    5400
attcagcagg gggtgaatct gaaagaggaa gacttcaata aagatatgaa tgaagacaat    5460
gagggtactg taaaagaatt gttgcaaaga ggagacaact acaacaaag aatcacagat    5520
gagagaaagc gagaggaaat aaagataaaa cagcagctgt tacagacaaa acataatgct    5580
ctcaaggatt tgaggtctca aagaagaaaa aaggctctag aaatttctca tcagtggtat    5640
cagtacaaga ggcaggctga tgatctcctg aaatgcttgg atgacattga aaaaaaatta    5700
gccagcctac ctgagcccag agatgaaagg aaaataaagg aaattgatcg ggaattgcag    5760
aagaagaaag aggagctgaa tgcagtgcgt aggcaagctg agggcttgtc tgaggatggg    5820
gccgcaatgg cagtggagcc aactcagatc cagctcagca agcgctggcg ggaaattgag    5880
agcaaatttg ctcagtttcg aagactcaac tttgcacaaa ttcacactgt ccgtgaagaa    5940
acgatgatgg tgatgactga agacatgcct ttggaaattt cttatgtgcc ttctacttat    6000
ttgactgaaa tcactcatgt ctcacaagcc ctattagaag tggaacaact tctcaatgct    6060
cctgacctct gtgctaagga cttttgaagat ctctttaagc aagaggagtc tctgaagaat    6120
ataaaagata gtctacaaca aagctcaggt cggattgaca ttattcatag caagaagaca    6180
gcagcattgc aaagtgcaac gcctgtggaa agggtgaagc tacaggaagc tctctcccag    6240
cttgatttcc aatgggaaaa agttaacaaa atgtacaagg accgacaagg gcgatttgac    6300
agatctgttg agaaatggcg gcgttttcat tatgatataa agatatttaa tcagtggcta    6360
acagaagctg aacagtttct cagaaagaca caaattcctg agaattggga acatgctaaa    6420
tacaaatggt atcttaagga actccaggat ggcattgggc agcggcaaac tgttgtcaga    6480
acattgaatg caactgggga agaataatt cagcaatcct caaaaacaga tgccagtatt    6540
ctacaggaaa aattgggaag cctgaatctg cggtggcagg aggtctgcaa acagctgtca    6600
gacagaaaaa agaggctaga agaacaaaag aatatcttgt cagaatttca aagagattta    6660
aatgaatttg ttttatggtt ggaggaagca gataacattg ctagtatccc acttgaacct    6720
ggaaaagagc agcaactaaa agaaaagctt gagcaagtca agttactggt ggaagagttg    6780
cccctgcgcc agggaattct caaacaatta atgaaactg gaggacccgt gcttgtaagt    6840
gctcccataa gcccagaaga gcaagataaa cttgaaaata agctcaagca gacaaatctc    6900
cagtggataa aggtttccag agctttacct gagaaacaag gagaaattga agctcaaata    6960
aaagaccttg ggcagcttga aaaaaagctt gaagaccttg aagagcagtt aaatcatctg    7020
ctgctgtggt tatctcctat taggaatcag ttggaaattt ataaccaacc aaaccaagaa    7080
ggaccatttg acgttcagga aactgaaata gcagttcaag ctaaacaacc ggatgtggaa    7140
gagattttgt ctaaagggca gcatttgtac aaggaaaaac cagccactca gccagtgaag    7200
aggaagttag aagatctgag ctctgagtgg aaggcggtaa accgtttact tcaagagctg    7260
agggcaaagc agcctgacct agctcctgga ctgaccacta ttggagcctc tcctactcag    7320
actgttactc tggtgacaca acctgtggtt actaaggaaa ctgccatctc caaactagaa    7380
atgccatctt ccttgatgtt ggaggtacct gctctggcag atttcaaccg gcttggaca    7440
gaacttaccg actggctttc tctgcttgat caagttataa aatcacagag ggtgatggtg    7500
ggtgaccttg aggatatcaa cgagatgatc atcaagcaga aggcaacaat gcaggatttg    7560
gaacagaggc gtccccagtt ggaagaactc attaccgctg cccaaaattt gaaaaacaag    7620
```

```
accagcaatc aagaggctag aacaatcatt acggatcgaa ttgaaagaat tcagaatcag    7680
tgggatgaag tacaagaaca ccttcagaac cggaggcaac agttgaatga aatgttaaag    7740
gattcaacac aatggctgga agctaaggaa gaagctgagc aggtcttagg acaggccaga    7800
gccaagcttg agtcatggaa ggagggtccc tatacagtag atgcaatcca aaagaaaatc    7860
acagaaacca agcagttggc caaagacctc cgccagtggc agacaaatgt agatgtggca    7920
aatgacttgg ccctgaaact tctccgggat tattctgcag atgataccag aaaagtccac    7980
atgataacag agaatatcaa tgcctcttgg agaagcattc ataaaagggt gagtgagcga    8040
gaggctgctt tggaagaaac tcatagatta ctgcaacagt tccccctgga cctggaaaag    8100
tttcttgcct ggcttacaga agctgaaaca actgccaatg tcctacagga tgctacccgt    8160
aaggaaaggc tcctagaaga ctccaaggga gtaaaagagc tgatgaaaca atggcaagac    8220
ctccaaggtg aaattgaagc tcacacagat gtttatcaca acctggatga aaacagccaa    8280
aaaatcctga gatccctgga aggttccgat gatgcagtcc tgttacaaag acgtttggat    8340
aacatgaact tcaagtggag tgaacttcgg aaaaagtctc tcaacattag gtcccatttg    8400
gaagccagtt ctgaccagtg gaagcgtctg ccctttctc tgcaggaact tctggtgtgg    8460
ctacagctga agatgatga attaagccgg caggcaccta ttggaggcga cttttccagca   8520 gttcagaagc agaacgatgt acatagggcc ttcaagaggg aattgaaaac taaagaacct    8580
gtaatcatga gtactcttga gactgtacga atatttctga cagagcagcc tttggaagga    8640
ctagagaaac tctaccagga gcccagagag ctgcctcctg aggagagagc ccagaatgtc    8700
actcggcttc tacgaaagca ggctgaggag gtcaatactg agtgggaaaa attgaacctg    8760
cactccgctg actggcagag aaaaatagat gagacccttg aaagactcca ggaacttcaa    8820
gaggccacgg atgagctgga cctcaagctg cgccaagctg aggtgatcaa gggatcctgg    8880
cagcccgtgg gcgatctcct cattgactct ctccaagatc acctcgagaa agtcaaggca    8940
cttcgaggag aaattgcgcc tctgaaagag aacgtgagcc acgtcaatga ccttgctcgc    9000
cagcttacca cttgggcat tcagctctca ccgtataacc tcagcactct ggaagacctg    9060
aacaccagat ggaagcttct gcaggtggcc gtcgaggacc gagtcaggca gctgcatgaa    9120
gcccacaggg actttggtcc agcatctcag cactttcttt ccacgtctgt ccagggtccc    9180
tgggagagag ccatctcgcc aaacaaagtg ccctactata tcaaccacga gactcaaaca    9240
acttgctggg accatcccaa aatgacagag ctctaccagt ctttagctga cctgaataat    9300
gtcagattct cagcttatag gactgccatg aaactccgaa gactgcagaa ggcccctttgc    9360 ttggatctct tgagcctgtc agctgcatgt gatgccttgg accagcacaa cctcaagcaa    9420
aatgaccagc ccatggatat cctgcagatt attaattgtt tgaccactat ttatgaccgc    9480
ctggagcaag agcacaacaa tttggtcaac gtccctctct gcgtggatat gtgtctgaac    9540
tggctgctga atgtttatga tacgggacga acagggagga tccgtgtcct gtcttttaaa    9600
actggcatca tttccctgtg taaagcacat ttggaagaca agtacagata ccttttcaag    9660
caagtggcaa gttcaacagg atttttgtgac cagcgcaggc tgggcctcct tctgcatgat    9720
tctatccaaa ttccaagaca gttgggtgaa gttgcatcct ttgggggcag taacattgag    9780
ccaagtgtcc ggagctgctt ccaatttgct aataataagc cagagatcga agcggccctc    9840
ttcctagact ggatgagact ggaacccag tccatggtgt ggctgcccgt cctgcacaga    9900
gtggctgctg cagaaactgc caagcatcag gccaaatgta acatctgcaa agagtgtcca    9960
```

```
atcattggat tcaggtacag gagtctaaag cactttaatt atgacatctg ccaaagctgc    10020 ttttttctg  gtcgagttgc  aaaaggccat  aaaatgcact  atcccatggt  ggaatattgc    10080
actccgacta catcaggaga agatgttcga gactttgcca aggtactaaa aaacaaattt    10140
cgaaccaaaa ggtattttgc gaagcatccc cgaatgggct acctgccagt gcagactgtc    10200 ttagagggg  acaacatgga  aactcccgtt  actctgatca  acttctggcc  agtagattct    10260
gcgcctgcct cgtcccctca gctttcacac gatgatactc attcacgcat tgaacattat    10320
gctagcaggc tagcagaaat ggaaaacagc aatggatctt atctaaatga tagcatctct    10380
cctaatgaga gcatagatga tgaacatttg ttaatccagc attactgcca aagtttgaac    10440
caggactccc ccctgagcca gcctcgtagt cctgcccaga tcttgatttc cttagagagt    10500
gaggaaagag gggagctaga gagaatccta gcagatcttg aggaagaaaa caggaatctg    10560
caagcagaat atgaccgtct aaagcagcag cacgaacata aaggcctgtc cccactgccg    10620
tcccctcctg aaatgatgcc cacctctccc cagagtcccc gggatgctga gctcattgct    10680
gaggccaagc tactgcgtca acacaaaggc cgcctggaag ccaggatgca aatcctggaa    10740
gaccacaata aacagctgga gtcacagtta cacaggctaa ggcagctgct ggagcaaccc    10800
caggcagagg ccaaagtgaa tggcacaacg gtgtcctctc cttctacctc tctacagagg    10860
tccgacagca gtcagcctat gctgctccga gtggttggca gtcaaacttc ggactccatg    10920
ggtgaggaag atcttctcag tcctccccag gacacaagca cagggttaga ggaggtgatg    10980
gagcaactca acaactcctt ccctagttca agaggaagaa ataccctgg  aaagccaatg    11040 agagaggaca caatgtagga agtcttttcc acatggcaga tgatttgggc agagcgatgg    11100
agtccttagt atcagtcatg acagatgaag aaggagcaga ataaatgttt tacaactcct    11160
gattcccgca tggttttat  aatattcata caacaaagag gattagacag taagagttta    11220
caagaaataa atctatattt ttgtgaaggg tagtggtatt atactgtaga tttcagtagt    11280
ttctaagtct gttattgttt tgttaacaat ggcaggtttt acacgtctat gcaattgtac    11340
aaaaaagtta taagaaaact acatgtaaaa tcttgatagc taaataactt gccatttctt    11400
tatatggaac gcattttggg ttgtttaaaa atttataaca gttataaaga aagattgtaa    11460
actaaagtgt gctttataaa aaaaagttgt ttataaaaac ccctaaaaac aaaacaaaca    11520
cacacacaca cacatacaca cacacacaca aaactttgag gcagcgcatt gttttgcatc    11580
cttttggcgt gatatccata tgaaattcat ggcttttttct ttttttgcat attaaagata    11640
agacttcctc taccaccaca ccaaatgact actacacact gctcatttga gaactgtcag    11700
ctgagtgggg caggcttgag ttttcatttc atatatctat atgtctataa gtatataaat    11760
actatagtta tatagataaa gagatacgaa tttctataga ctgactttttt ccattttta    11820 aatgttcatg tcacatccta atagaaagaa attacttcta gtcagtcatc caggcttacc    11880
tgcttggtct agaatggatt tttcccggag ccggaagcca ggaggaaact acaccacact    11940
aaaacattgt ctacagctcc agatgtttct catttttaaac aactttccac tgacaacgaa    12000
agtaaagtaa agtattggat ttttttaaag ggaacatgtg aatgaataca caggacttat    12060
tatatcagag tgagtaatcg gttggttggt tgattgattg attgattgat acattcagct    12120
tcctgctgct agcaatgcca cgatttagat ttaatgatgc ttcagtggaa atcaatcaga    12180
aggtattctg accttgtgaa catcagaagg tattttttaa ctcccaagca gtagcaggac    12240
gatgataggg ctggagggct atggattccc agcccatccc tgtgaaggag taggccactc    12300
tttaagtgaa ggattggatg attgttcata atacataaag ttctctgtaa ttacaactaa    12360
```

-continued

```
attattatgc cctcttctca cagtcaaaag gaactgggtg gtttggtttt tgttgctttt    12420
ttagatttat tgtcccatgt gggatgagtt tttaaatgcc acaagacata atttaaaata    12480
aataaacttt gggaaaaggt gtaaaacagt agccccatca catttgtgat actgacaggt    12540
atcaacccag aagcccatga actgtgtttc catcctttgc atttctctgc gagtagttcc    12600
acacaggttt gtaagtaagt aagaagaag gcaaattgat tcaaatgtta caaaaaaacc    12660
cttcttggtg gattagacag gttaaatata aaacaaaca aacaaaaatt gctcaaaaaa    12720
gaggagaaaa gctcaagagg aaaagctaag gactggtagg aaaaagcttt actctttcat    12780 gccatttat ttcttttga ttttaaatc attcattcaa tagataccac cgtgtgacct      12840
ataattttgc aaatctgtta cctctgacat caagtgtaat tagcttttgg agagtgggct    12900
gacatcaagt gtaattagct tttggagagt gggttttgtc cattattaat aattaattaa    12960
ttaacatcaa acacggcttc tcatgctatt tctacctcac tttggttttg gggtgttcct    13020
gataattgtg cacacctgag ttcacagctt caccacttgt ccattgcgtt attttctttt    13080
tcctttataa ttcttctttt ttccttcata attttcaaaa gaaaacccaa agctctaagg    13140
taacaaatta ccaaattaca tgaagatttg gttttgtct tgcattttt tccttatgt      13200 gacgctggac cttttcttta cccaaggatt tttaaaactc agatttaaaa caaggggtta    13260
ctttacatcc tactaagaag tttaagtaag taagttcat tctaaaatca gaggtaaata    13320
gagtgcataa ataattttgt tttaatcttt ttgttttct tttagacaca ttagctctgg    13380
agtgagtctg tcataatatt tgaacaaaaa ttgagagctt tattgctgca tttttaagcat   13440 aattaatttg gacattattt cgtgttgtgt tctttataac caccaagtat taaactgtaa    13500
atcataatgt aactgaagca taaacatcac atggcatgtt ttgtcattgt tttcaggtac    13560
tgagttctta cttgagtatc ataatatatt gtgttttaac accaacactg taacatttac    13620
gaattatttt tttaaacttc agttttactg cattttcaca acatatcaga cttcaccaaa    13680
tatatgcctt actattgtat tatagtactg ctttactgtg tatctcaata aagcacgcag    13740
ttatgttac                                                          13749
```

<210> SEQ ID NO 2
<211> LENGTH: 21
<212> TYPE: DNA
<213> ORGANISM: Artificial
<220> FEATURE:
<223> OTHER INFORMATION: forward c27f

<400> SEQUENCE: 2
cctgtagcac aagaggcctt a                                              21

<210> SEQ ID NO 3
<211> LENGTH: 22
<212> TYPE: DNA
<213> ORGANISM: Artificial
<220> FEATURE:
<223> OTHER INFORMATION: reverse 2F

<400> SEQUENCE: 3
tccacactct ttgtttccaa tg                                             22

<210> SEQ ID NO 4
<211> LENGTH: 28
<212> TYPE: DNA
<213> ORGANISM: Artificial
<220> FEATURE:

```
<223> OTHER INFORMATION: intron 30f-NheI

<400> SEQUENCE: 4
gcggctagcg tgatccacct gcctcgac                                              28

<210> SEQ ID NO 5
<211> LENGTH: 29
<212> TYPE: DNA
<213> ORGANISM: Artificial
<220> FEATURE:
<223> OTHER INFORMATION: intron 31r-BamHI

<400> SEQUENCE: 5
gcgggatcct caaatccaat cttgccaat                                             29

<210> SEQ ID NO 6
<211> LENGTH: 35
<212> TYPE: DNA
<213> ORGANISM: Artificial
<220> FEATURE:
<223> OTHER INFORMATION: intron 26f-NheI

<400> SEQUENCE: 6
gcggctagca aatttatgga agagactgga gttca                                      35

<210> SEQ ID NO 7
<211> LENGTH: 31
<212> TYPE: DNA
<213> ORGANISM: Artificial
<220> FEATURE:
<223> OTHER INFORMATION: intron 27r-BamHI

<400> SEQUENCE: 7
gcgggatccc aagttaagca aatggcccaa a                                          31
```